US008034935B2

(12) United States Patent
Igarashi et al.

(10) Patent No.: US 8,034,935 B2
(45) Date of Patent: *Oct. 11, 2011

(54) LIGHT-EMITTING MATERIAL COMPRISING ORTHOMETALATED IRIDIUM COMPLEX, LIGHT-EMITTING DEVICE, HIGH EFFICIENCY RED LIGHT-EMITTING DEVICE, AND NOVEL IRIDIUM COMPLEX

(75) Inventors: Tatsuya Igarashi, Ashigara (JP); Keizo Kimura, Kanagawa (JP); Kazumi Nii, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/957,144

(22) Filed: Nov. 30, 2010

(65) Prior Publication Data

US 2011/0071292 A1 Mar. 24, 2011

Related U.S. Application Data

(60) Division of application No. 12/725,025, filed on Mar. 16, 2010, now abandoned, which is a continuation of application No. 11/802,492, filed on May 23, 2007, which is a continuation of application No. 10/844,394, filed on May 13, 2004, now Pat. No. 7,238,437, which is a division of application No. 09/747,933, filed on Dec. 27, 2000, now Pat. No. 6,821,645.

(30) Foreign Application Priority Data

Dec. 27, 1999 (JP) .................................. 11-370349
Mar. 28, 2000 (JP) ................................. 2000-089274
Sep. 29, 2000 (JP) ................................. 2000-298470
Sep. 29, 2000 (JP) ................................. 2000-299495

(51) Int. Cl.
*C07F 15/00* (2006.01)
(52) U.S. Cl. .................................. 546/10; 546/2; 546/4
(58) Field of Classification Search .................... 546/10, 546/4, 2
See application file for complete search history.

(56) References Cited

U.S. PATENT DOCUMENTS

| | | | |
|---|---|---|---|
| 5,698,858 A | 12/1997 | Borner | |
| 5,756,224 A | 5/1998 | Borner et al. | |
| 6,310,360 B1 | 10/2001 | Forrest et al. | |
| 6,635,364 B1 | 10/2003 | Igarashi | |
| 6,656,608 B1 | 12/2003 | Kita et al. | |
| 6,821,645 B2 | 11/2004 | Igarashi et al. | |
| 6,821,646 B2 | 11/2004 | Tsuboyama et al. | |
| 6,902,830 B2 | 6/2005 | Thompson et al. | |
| 7,147,935 B2 | 12/2006 | Kamatani et al. | |
| 2002/0034656 A1 | 3/2002 | Thompson et al. | |
| 2002/0121638 A1 | 9/2002 | Grushin et al. | |
| 2002/0190250 A1 | 12/2002 | Grushin et al. | |
| 2003/0096138 A1 | 5/2003 | Lecloux et al. | |

FOREIGN PATENT DOCUMENTS

| | | |
|---|---|---|
| JP | 8-319482 A | 12/1996 |
| JP | 2001-143869 A | 5/2001 |
| JP | 2003-515897 A | 5/2003 |
| JP | 2003-526876 A | 9/2003 |
| JP | 2004-503059 A | 1/2004 |
| WO | 00/70655 A2 | 11/2000 |
| WO | 01/41512 A1 | 6/2001 |

OTHER PUBLICATIONS

Baldo, et al., "Very high-efficiency green organic light-emitting devices based on electrophosphorescence," *Applied Physics Letters* 75 (1):4-6 (1999).
Maestri, et al., "Photochemistry and Luminescence of Cyclometalated Complexes, "*Advances in Photochemistry* 17:1-68 (1992).
Tsutsui, et al., "High Quantum Efficiency in Organic Light-Emitting-Devices with Iridium-Complex as a Triplet Emissive Center," *Jpn. J. Appl. Phys.* 38:L1502-L1504 (1999).
Nonoyama, M.: Benzo[h]quinolin-10-yl-N Iridium (iii) complexes. Bull. Chem. Soc. Jpn., vol. 47, pp. 767-768, 1974.
Lamansky et al, "Highly Phosphorescent Bis-Cyclometalated Iridium Complexes: Synthesis, Photophysical Characterization, and use in Organic Light Emitting Diodes", J. Am. Chem. Soc., 123:4304-4312 (2001).
2000 International Chemical Congress of Pacific Basin Societies, Macromolecular Chemistry, Abstracts 1-14 and Phys 10, Abstracts 142-148, Conference in Honolulu (Dec. 14-19, 2000).
Miyaguchi, "Development Progress of Organic Electroluminescent Display", 68th Annual Meeting of Japan of Electric Conversion Academic Society, p. 281 (2001), Concise Statement.
Ohmori, "Recent Progress of Organic Electroluminescent Display and Devices", Electric information American Communications Association Comprehensive Conference, pp. 205-206 (2001), Concise Statement.

(Continued)

*Primary Examiner* — Charanjit Aulakh
(74) *Attorney, Agent, or Firm* — Sughrue Mion, PLLC

(57) ABSTRACT

A synthesis method of a compound represented by following formula (24), the method comprising reacting at least one of a ligand and a dissociation product thereof with an iridium compound at a room temperature or at an elevated temperatures in the presence or absence of a solvent or in the presence or absence of a base:

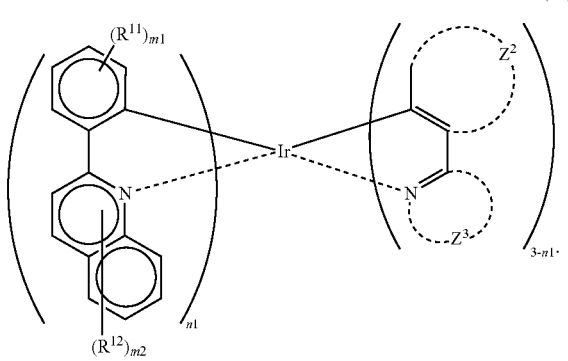

(24)

6 Claims, No Drawings

OTHER PUBLICATIONS

Aso, "Present Condition and Material Development of Organic Electro-Luminescence Element", 34th Chemical Conference in Chugoku/Shikoku Branch of the Chemical Society of Japan, pp. 1-5 (Apr. 20, 2001), Concise Statement.

Tanaka et al., "Organic EL Devices on Ir Complex-Doped Poly(N-vinylcarbazole)", 48th Meeting of the Japan Society of Applied Physics and Related Societies, Meiji University, p. 1284 (Mar. 2001), Concise Statement.

Hamada, "Development for the Organic Materials for OLEDs", Electric information American Communications Association Comprehensive Conference, pp. 211-212 (2001), Concise Statement.

Information Offer Form, listing submitted publications or the like, dated Feb. 14, 2008 in counterpart Japanese Application No. 2007-018365.

Notification of Reasons for Refusal issued Sep. 16, 2009 in counterpart Japanese Application No. 2007-018365.

Decision of Refusal issued Sep. 28, 2010 in counterpart Japanese Application No. 2007-018365.

Excerpt from U.S. Appl. No. 09/452,346, filed Dec. 1, 1999, pp. 3, 4, 12, 17 and Fig. 39.

Ma, Y., et al., "Electroluminescence from triplet metal-ligand charge-transfer excited state of transition metal complexes", Synthetic Metals, 1998, pp. 245-248, vol. 94.

LIGHT-EMITTING MATERIAL COMPRISING ORTHOMETALATED IRIDIUM COMPLEX, LIGHT-EMITTING DEVICE, HIGH EFFICIENCY RED LIGHT-EMITTING DEVICE, AND NOVEL IRIDIUM COMPLEX

CROSS REFERENCE TO RELATED APPLICATION

This application is a divisional of pending U.S. application Ser. No. 12/725,025 filed on Mar. 16, 2010, which is a continuation of U.S. application Ser. No. 11/802,492 filed May 23, 2007, which is a continuation of U.S. application Ser. No. 10/844,394 filed on May 13, 2004, now U.S. Pat. No. 7,238,437, which is a divisional of U.S. application Ser. No. 09/747,933 filed Dec. 27, 2000 now U.S. Pat. No. 6,821,645, the disclosures of which are incorporated herein by reference.

BACKGROUND OF THE INVENTION

1. Field of the Invention

The present invention relates to a light-emitting material (i.e., a light-emitting device material) and light-emitting device capable of converting electric energy to light which is then emitted and more particularly to a light-emitting device which can be preferably used in various arts such as display device, display, backlight, electrophotography, illuminating light source, recording light source, exposure light source, reading light source, sign, advertising display and interior. The present invention also relates to a novel light-emitting material which can be expected to find application in various arts.

2. Description of the Related Art

Today, various display devices have been under active study and development. In particular, an organic electric field light-emitting (EL) device can emit with a high luminance at a low voltage and thus has been noted as a favorable display device. For example, a light-emitting device having a vacuum-deposited thin organic layer has been known (Applied Physics Letters, vol. 51, page 913, 1987). The light-emitting device described in this reference comprises as an electron-transporting material tris(8-hydroxyquinolinate) aluminum complex (Alq) which is laminated with a positive hole-transporting material (amine compound) to exhibit drastically improved light-emitting properties as compared with the conventional single-layer type devices.

In recent years, the application of organic EL device to color display has been under active study. However, in order to develop a high performance color display, it is necessary that the properties of blue, green and red light-emitting devices be each improved.

As a means for improving the properties of light-emitting devices there has been reported a green light-emitting device utilizing the emission of light from orthometalated iridium complex (Ir(ppy)$_3$: Tris-Ortho-Metalated Complex of Iridium (III) with 2-Phenylpyridine) (Applied Physics Letters 75, 4 (1999)). The foregoing device can attain an external quantum yield of 8%, which is higher than the limit of the external quantum yield of the conventional light-emitting devices, i.e., 5%. However, since the foregoing light-emitting device is limited to green light-emitting device, the range within it can be applied as a display is narrow. It has thus been desired to develop light-emitting materials capable of emitting light having other colors.

Noting a red light-emitting device, many light-emitting devices comprising DCM(4-(Dicyanomethylene)-2-methyl-6-(4-dimethylaminostyryl)-4H-pyran) and its analogy have been reported. No devices having an external quantum efficiency of more than 5% have been reported. If the external quantum efficiency of 5%, which is considered to be the limit of the external efficiency of the conventional red light-emitting device, can be surpassed, the development of high efficiency organic EL devices capable of emitting light having various colors can make a great progress. It has thus been desired to develop such high efficiency organic EL devices.

On the other hand, an organic light-emitting device which can attain light emission with a high luminance is one having a laminate of vacuum-deposited organic material layers. The preparation of such a device is preferably accomplished by a coating method from the standpoint of simplification of production procedure, workability, area attained, etc. However, the device prepared by the conventional coating method is inferior to that prepared by vacuum evaporation method particularly in light-emitting efficiency. It has thus been desired to develop a novel light-emitting material.

In recent years, various materials having fluorescence have been used in various arts such as filter dye, color conversion filter, dye for photographic material, sensitizing dye, dye for dyeing pulp, laser dye, fluorescent medicine for medical diagnosis and organic light-emitting material. Thus, there is a growing demand for such a material. New light-emitting materials have been desired.

SUMMARY OF THE INVENTION

An object of the present invention is to provide a light-emitting device having good light-emitting properties, a light-emitting material which can form such a light-emitting device, and a novel light-emitting material which can be used in various fields. (a first embodiment)

Another object of the present invention is to provide a red light-emitting device having good light-emitting properties, a light-emitting material which can form such a light-emitting device, and a novel light-emitting material which can be used in various fields. (a second embodiment)

The foregoing object of the invention can be accomplished by the following means.

1. A light-emitting material comprising a compound having a partial structure represented by the following formulae (1) to (10), (21), (22), or tautomer thereof:

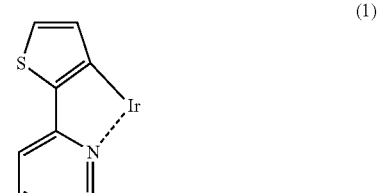

(1)

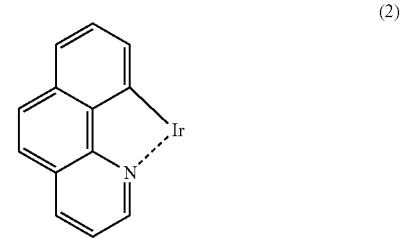

(2)

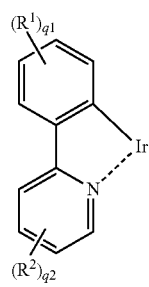
(3)

wherein $R^1$ and $R^2$ each represent a substituent; and $q^1$ and $q^2$ each represent an integer of from 0 to 4, with the proviso that the sum of $q^1$ and $q^2$ is 1 or more,

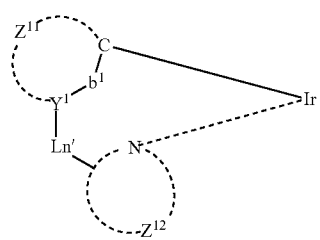
(4)

wherein $Z^{11}$ and $Z^{12}$ each represent a nonmetallic atom group required to form a 5- or 6-membered ring with at least one of carbon atom and nitrogen atom, said ring optionally having a substituent or forming a condensed ring with the other ring; $Ln^1$ represents a divalent group; $Y^1$ represents a nitrogen atom or carbon atom; and $b^1$ represents a single bond or double bond, (CO) Ir (5)

(NC) Ir (6)

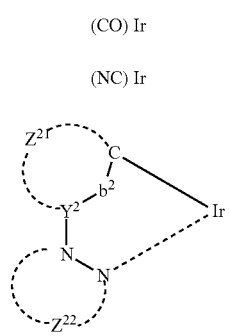
(7)

wherein $Z^{21}$ and $Z^{22}$ each represent a nonmetallic atom group required to form a 5- or 6-membered ring with at least one of carbon atom and nitrogen atom, said ring optionally having a substituent or forming a condensed ring with the other ring; $Y^2$ represents a nitrogen atom or carbon atom; and $b^2$ represents a single bond or double bond,

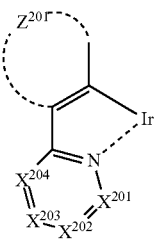
(8)

wherein $X^{201}$, $X^{202}$, $X^{203}$ and $X^{204}$ each represent a nitrogen atom or C—R and forms a nitrogen-containing heteroaryl 6-membered ring with —C=N—, with the proviso that at least one of $X^{201}$, $X^{202}$, $X^{203}$ and $X^{204}$ represents a nitrogen atom; R represents a hydrogen atom or substituent; and $Z^{201}$ represents an atomic group for forming an aryl or heteroaryl ring,

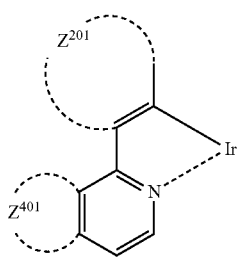
(9)

wherein $Z^{201}$ and $Z^{301}$ each represent an atomic group for forming an aryl or heteroaryl ring, (10)

wherein $Z^{201}$ and $Z^{401}$ each represent an atomic group for forming an aryl or heteroaryl ring,

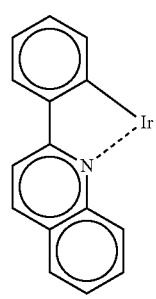
(21)

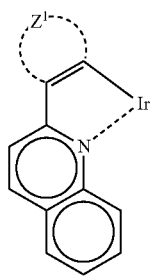
(22)

wherein $Z^1$ represents an atomic group which forms a heteroaryl ring.

2. The light-emitting material according to item 1, which comprises the compound represented by the formula (21) or (22), wherein said quinoline derivative ligand is formed by at least four rings.

3. A compound having a partial structure represented by the following formula (4) or a tautomer thereof:

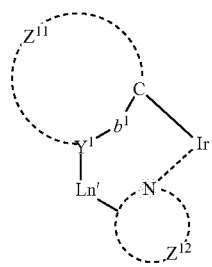
(4)

wherein $Z^{11}$ and $Z^{12}$ each represent a nonmetallic atom group required to form a 5- or 6-membered ring with carbon atom and/or nitrogen atom, said ring optionally having a substituent or forming a condensed ring with the other ring; $Ln^1$ represents a divalent group; $Y^1$ represents a nitrogen atom or carbon atom; and $b^1$ represents a single bond or double bond.

4. A compound represented by the following formula (23) or (24):

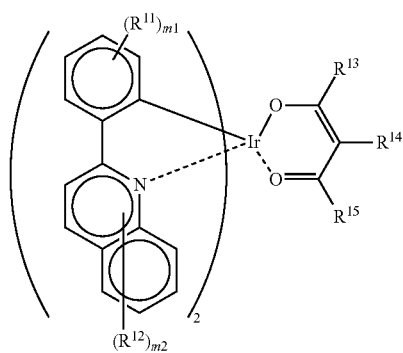
(23)

wherein $R^{11}$ and $R^{12}$ each represent a substituent; $R^{13}$, $R^{14}$ and $R^{15}$ each represent a hydrogen atom or substituent; $m^1$ represents an integer of from 0 to 4; and $m^2$ represents an integer of from 0 to 6,

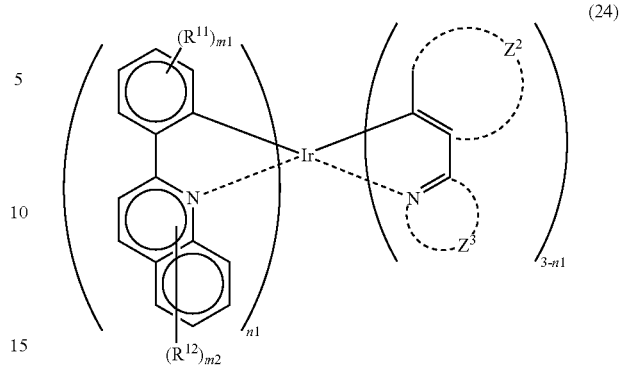
(24)

wherein $R^{11}$ and $R^{12}$ each represent a substituent; $m^1$ represents an integer of from 0 to 4; $m^2$ represents an integer of from 0 to 6; $Z^2$ represents an atomic group which forms an aryl or heteroaryl ring; $Z^3$ represents an atomic group which forms a nitrogen-containing heteroaryl ring; and $n^1$ represents an integer of from 1 to 3.

5. An organic light-emitting device comprising a light-emitting layer or a plurality of thin organic compound layers containing a light-emitting layer formed interposed between a pair of electrodes, wherein at least one layer comprises a light-emitting material having a partial structure represented by the following formula (1) to (10), (21), (22) or a tautomer thereof:

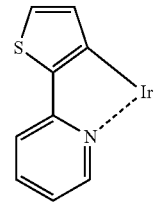
(1)

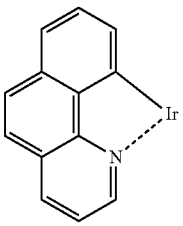
(2)

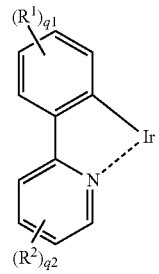
(3)

wherein $R^1$ and $R^2$ each represent a substituent; and $q^1$ and $q^2$ each represent an integer of from 0 to 4, with the proviso that the sum of $q^1$ and $q^2$ is 1 or more, (4)

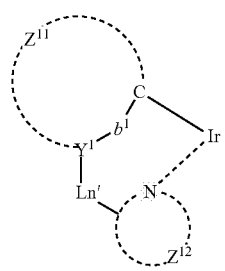

wherein $Z^{11}$ and $Z^{12}$ each represent a nonmetallic atom group required to form a 5- or 6-membered ring with at least one of carbon atom and nitrogen atom, said ring optionally having a substituent or forming a condensed ring with the other ring; $Ln^1$ represents a divalent group; $Y^1$ represents a nitrogen atom or carbon atom; and $b^1$ represents a single bond or double bond, (5)
(CO)Ir (6)
(NC)Ir (7)

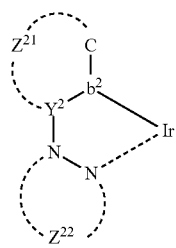

wherein $Z^{21}$ and $Z^{22}$ each represent a nonmetallic atom group required to form a 5- or 6-membered ring with at least one of carbon atom and nitrogen atom, said ring optionally having a substituent or forming a condensed ring with the other ring; $Y^2$ represents a nitrogen atom or carbon atom; and $b^2$ represents a single bond or double bond, (8)

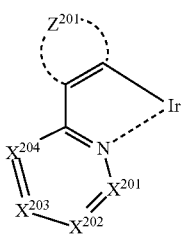

wherein $X^{201}$, $X^{202}$, $X^{203}$ and $X^{204}$ each represent a nitrogen atom or C—R and forms a nitrogen-containing heteroaryl 6-membered ring with —C=N—, with the proviso that at least one of $X^{201}$, $X^{202}$, $X^{203}$ and $X^{204}$ represents a nitrogen atom; R represents a hydrogen atom or substituent; and $Z^{201}$ represents an atomic group for forming an aryl or heteroaryl ring, (9)

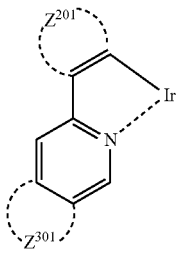

wherein $Z^{201}$ and $Z^{301}$ each represent an atomic group for forming an aryl or heteroaryl ring, (10)

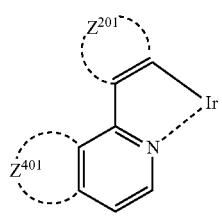

wherein $Z^{201}$ and $Z^{401}$ each represent an atomic group for forming an aryl or heteroaryl ring, (21)

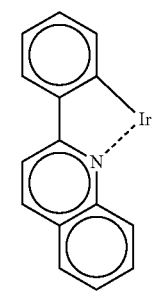

(22)

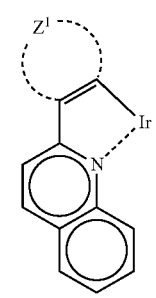

wherein $Z^1$ represents an atomic group which forms a heteroaryl ring.

6. An organic light-emitting device according to item 5, wherein at least one layer consists essentially of the light-emitting material.

7. The light-emitting device according to item 5, wherein said layer comprising the light-emitting material is formed by a coating process.

8. An organic light-emitting device comprising a light-emitting layer or a plurality of thin organic compound layers containing a light-emitting layer formed interposed between a pair of electrodes, wherein at least one layer contains an orthometalated iridium complex, and said layer containing an orthometalated iridium complex is formed by a coating process.

9. An organic light-emitting device having an external quantum efficiency of 5% or more, and a λmax of light emitting of 590 nm or more.

DETAILED DESCRIPTION OF THE INVENTION

The first embodiment of the present invention will be further described hereinafter.

The compound according to the invention is a light-emitting material comprising an orthometalated iridium complex. "Orthometalated metal complex" is a generic term for a group of compounds as described in Akio Yamamoto, "Yuki Kinzoku Kagaku-Kiso to Oyo—(Organic Metal Chemistry—Fundamentals and Application)", Shokabosha, pp. 150, 232, 1982, H. Yersin, "Photochemistry and Photophysics of Coordination Compounds", Springer-Verlag, pp. 1-77, pp. 135-146, 1987, etc.

The valence of iridium in the orthometalated iridium complex is not specifically limited but is preferably 3. The ligands constituting the orthometalated iridium complex are not specifically limited so far as they can form an orthometalated complex. In practice, however, there may be used, e.g., aryl group-substituted nitrogen-containing heterocyclic derivative (The aryl group substitutes for the nitrogen-containing heterocycle on the carbon atom adjacent to nitrogen atom. Examples of the aryl group include phenyl group, naphthyl group, anthryl group, phenanthryl group, and pyrenyl group. The aryl group may further form a condensed ring with other carbon rings or heterocycles. Examples of the nitrogen-containing heterocycle include pyridine, pyrimidine, pyrazine, pyridazine, quinoline, isoquinoline, quinoxaline, phthalazine, quinazoline, naphtholidine, cinnoline, perimidine, phenanthroline, pyrrole, imidazole, pyrazole, oxazole, oxadiazole, triazole, thiadiazole, benzimidazole, benzoxazole, and phenanthridine), heteroaryl group-substituted nitrogen-containing heterocyclic derivative (The heteroaryl group substitutes for the nitrogen-containing heterocycle on the carbon atom adjacent to nitrogen atom. Examples of the heteroaryl group include group containing the foregoing nitrogen-containing heterocyclic derivative, chenyl group, and furyl group), 7,8-benzoquinoline derivative, phosphinoaryl derivative, phosphinoheteroaryl derivative, phosphinoxyaryl derivative, phosphinoxyheteroaryl derivative, aminomethylaryl derivative, aminomethylheteroaryl derivative, etc. Preferred among these ligands are aryl group-substituted nitrogen-containing aromatic heterocyclic derivative, heteroaryl group-substituted nitrogen-containing aromatic heterocyclic derivative, and 7,8-benzoquinoline derivative. Even more desirable among these ligands are phenylpyridine derivative, chenylpyridine derivative, 7,8-benzoquinoline derivative, benzylpyridine derivative, phenylpyrazole derivative, phenylisoquinoline derivative, and phenyl-substituted derivative of azole having two or more nitrogen atoms. Particularly preferred among these ligands are chenylpyridine derivative, 7,8-benzoquinoline derivative, benzylpyridine derivative, phenylpyrazole derivative, phenylisoquinoline derivative, and phenyl-substituted derivative of azole having two or more nitrogen atoms.

The compound of the invention may have ligands other than the ligands required to form an orthometalated complex. Examples of the other ligands include various known ligands. Examples of these ligands include those described in H. Yersin, "Photochemistry and Photophysics of Coordination Compounds", Springer-Verlag, 1987, Akio Yamamoto, "Yuki Kinzoku Kagaku-Kiso to Oyo—(Organic Metal Chemistry—Fundamentals and Application)", Shokabosha, 1992, etc. Preferred among these ligands are halogen ligands (preferably chlorine ligand), nitrogen-containing heterocyclic ligands (e.g., bipyridyl, phenanthroline), and diketone ligands. Even mare desirable among these ligands are chlorine ligand and bipyridyl ligand.

There may be used one or a plurality of kinds of ligands constituting the compound of the invention. The number of ligands in the complex is preferably from 1 to 3, particularly from 1 or 2, more preferably 1.

The number of carbon atoms in the compound of the invention is preferably from 5 to 100, more preferably from 10 to 80, even more preferably from 14 to 50.

Preferred among the compounds of the invention having a partial structure represented by the formulae (1) to (10) or tautomers thereof are those having a partial structure represented by the formulae (1), (2), (4) to (10) or tautomers thereof.

The compound having a partial structure represented by the formula (1) or tautomer thereof may have one iridium atom per molecule or may be a so-called binuclear complex having two or more iridium atoms per molecule. This compound may further contain other metal atoms. This can apply to the compounds having a partial structure represented by the formula (2) to (10) or tautomers thereof.

In the formula (3), $R^1$ and $R^2$ each represents a substituent. The suffixes $q^1$ and $q^2$ each represent an integer of from 0 to 4, with the proviso that the sum-of $q^1$ and $q^2$ is 1 or more. When $q^1$ and $q^2$ each are 2 or more, the plurality of $R^1$'s and $R^2$'s may be the same or different.

Examples of the group represented by $R^1$ or $R^2$ include alkyl group (alkyl group preferably having from 1 to 30, more preferably from 1 to 20, particularly from 1 to 10 carbon atoms, e.g., methyl, ethyl, iso-propyl, tert-butyl, n-octyl, n-decyl, n-hexadecyl, cyclopropyl, cyclopentyl, cyclohexyl, trifluoromethyl, pentafluoroethyl), alkenyl group (alkenyl group preferably having from 2 to 30 carbon atoms, more preferably from 2 to 20 carbon atoms, particularly from 2 to 10 carbon atoms, e.g., vinyl, allyl, 2-butenyl, 3-pentenyl), alkinyl group (alkinyl group preferably having from 2 to 30 carbon atoms, more preferably from 2 to 20 carbon atoms, particularly from 2 to 10 carbon atoms, e.g., propargyl, 3-pentinyl), aryl group (aryl group preferably having from 6 to 30 carbon atoms, more preferably from 6 to 20 carbon atoms, particularly from 6 to 12 carbon atoms, e.g., phenyl, p-methylphenyl, naphthyl, anthranyl), amino group (amino group preferably having from 0 to 30 carbon atoms, more preferably from 0 to 20 carbon atoms, particularly from 0 to 10 carbon atoms, e.g., amino, methylamino, dimethylamino, diethylamino, dibenzylamino, diphenylamino, ditollylamino), alkoxy group (alkoxy group preferably having from 1 to 30 carbon atoms, more preferably from 1 to 20 carbon atoms, particularly from 1 to carbon atoms, e.g., methoxy, ethoxy, butoxy, 2-ethylhexyloxy), aryloxy group (aryloxy group preferably having from 6 to 30 carbon atoms, more preferably from 6 to 20 carbon atoms, particularly from 6 to 12 carbon atoms, e.g., phenyloxy, 1-naphthyloxy, 2-naphthyloxy), heteroaryloxy group (heteroaryloxy group preferably having from 1 to 30 carbon atoms, more preferably from 1 to 20 carbon atoms, particularly from 1 to 12 carbon atoms, e.g., pyridyloxy, pyrazyloxy, pyrimidyloxy, quinolyloxy), acyl group (acyl group preferably having from 1 to 30 carbon atoms, more preferably from 1 to 20 carbon atoms, particularly from 1 to 12 carbon atoms, e.g., acetyl, benzoyl, formyl, pivaloyl), alkoxycarbonyl group (alkoxycarbonyl group preferably having from 2 to 30 carbon atoms, more preferably from 2 to 20 carbon atoms, particularly from 2 to 12 carbon atoms, e.g., methoxycarbonyl, ethoxycarbonyl), aryloxycarbonyl group (aryloxycarbonyl group preferably having from 7 to 30 carbon atoms, more preferably from 7 to 20 carbon atoms, particularly from 7 to 12 carbon atoms, e.g., phenyloxycarbonyl), acyloxy group (acyloxy group preferably having from 2 to 30 carbon atoms, more preferably from 2 to 20 carbon atoms, particularly from 2 to 10 carbon atoms, e.g., acetoxy, benzoyloxy), acylamino group (acylamino group preferably having from 2 to 30 carbon atoms, more preferably 2 to 20 carbon atoms, particularly from 2 to 10 carbon atoms, e.g., acetylamino, benzoylamino), alkoxycarbonylamino group -(alkoxycarbonylamino group preferably having from 2 to 30 carbon atoms, more preferably 2 to 20 carbon atoms, particularly from 2 to 12 carbon atoms, e.g., methoxycarbonylamino), aryloxycarbonylamino group (aryloxycarbonylamino group preferably having from 7 to 30 carbon atoms, more preferably 7 to 20 carbon atoms, particularly from 7 to 12 carbon atoms, e.g., phenyloxycarbonylamino), sulfonylamino group (sulfonylamino group preferably having from 1 to 30 carbon atoms, more preferably 1 to 20 carbon atoms, particularly from 1 to 12 carbon atoms, e.g., methanesulfonylamino, benzenesulfonylamino), sulfamoyl group (sulfamoyl group preferably having from 2 to 30 carbon atoms, more preferably 2 to 20 carbon atoms, particularly from 2 to 10 carbon atoms, e.g., sulfamoyl, methylsulfamoyl, dimethylsulfamoyl, phenylsulfamoyl), carbamoyl group (carbamoyl group preferably having from 1 to 30 carbon atoms, more preferably 1 to 20 carbon atoms, particularly from 1 to 12 carbon atoms, e.g., carbamoyl, methylcarbamoyl, diethylcarbamoyl, phenylcarbamoyl), alkylthio group (alkylthio group preferably having from 1 to 30 carbon atoms, more preferably 1 to 20 carbon atoms, particularly from 1 to 12 carbon atoms, e.g., methylthio, ethylthio), arylthio group (arylthio group preferably having from 6 to 30 carbon atoms, more preferably 6 to 20 carbon atoms, particularly from 6 to 12 carbon atoms, e.g., phenylthio), heteroarylthio group (heteroarylthio group preferably having from 1 to 30 carbon atoms, more preferably 1 to 20 carbon atoms, particularly from 1 to 12 carbon atoms, e.g., pyridylthio, 2-benzimizolylthio, 2-benzoxazoylthio, 2-benzthiazolylthio), sulfonyl group (sulfonyl group preferably having from 1 to 30 carbon atoms, more preferably 1 to 20 carbon atoms, particularly from 1 to 12 carbon atoms, e.g., mesyl, tosyl), sulfinyl group (sulfinyl group preferably having from 1 to 30 carbon atoms, more preferably 1 to 20 carbon atoms, particularly from 1 to 12 carbon atoms, e.g., methanesulfinyl, benzenesulfinyl), ureide group (ureide group preferably having from 1 to 30 carbon atoms, more preferably 1 to 20 carbon atoms, particularly from 1 to 12 carbon atoms, e.g., ureide, methylureide, phenylureide), phosphoric acid amide group (phosphoric acid amide group preferably having from 1 to 30 carbon atoms, more preferably 1 to 20 carbon atoms, particularly from 1 to 12 carbon atoms, e.g., diethylphosphoric acid amide, phenylphosphoric acid amide), hydroxy group, mercapto group, halogen atom (e.g., fluorine atom, chlorine atom, bromine atom, iodine atom), cyano group, sulfo group, carboxyl group, nitro group, hydroxamic acid group, sulfino group, hydrazino group, imino group, heterocyclic group (heterocyclic group preferably having from 1 to 30 carbon atoms, more preferably from 1 to 12 carbon atoms, and containing as hetero atoms nitrogen atom, oxygen atom and sulfur atom, e.g., imidazolyl, pyridyl, quinolyl, furyl, chenyl, piperidyl, morpholino, benzoxazolyl, benzimidazolyl, and benzthiazolyl), and silyl group (silyl group preferably having from 3 to 40 carbon atoms, more preferably from 3 to 30 carbon atoms, particularly from 3 to 24 carbon atoms, e.g., trimethylsilyl, triphenylsilyl). These substituents may be further substituted. $R^1$'s or $R^2$'s may be connected to each other, or $R^1$ and $R^2$ may be connected to each other to form a condensed ring structure.

$R^1$ and $R^2$ each are preferably an alkyl group, aryl group, alkoxy group, amino group, cyano group or a group which forms a condensed ring structure when $R^1$ and $R^2$ are connected to each other. Preferred among these groups are alkyl group and group which forms a condensed ring structure when $R^1$ and $R^2$ are connected to each other. The suffixes $q^1$ and $q^2$ each are preferably 0, 1 or 2. More preferably, the sum of $q^1$ and $q^2$ is 1 or 2.

In the formula (4), $Z^{11}$ and $Z^{12}$ each represent a nonmetallic atom group required to form a 5- or 6-membered ring which may have a substituent or may further form a condensed ring with the other ring. Examples of the substituents include halogen atom, aliphatic group, aryl group, heterocyclic group, cyano, nitro, —$OR^{101}$, —$SR^{102}$, —$CO_2R^{103}$, —$OCOR^{104}$, —$NR^{105}R^{106}$, $CONR^{107}R^{108}$, —$SO_2R^{109}$, —$SO_2NR^{110}R^{111}$, —$NR^{112}CONR^{113}R^{114}$, —$NR^{115}CO_2R^{116}$, —$COR^{117}$, —$NR^{118}COR^{119}$, and —$NR^{120}SO_2R^{121}$ in which $R^{101}$, $R^{102}$, $R^{103}$, $R^{104}$, $R^{105}$, $R^{106}$, $R^{107}$, $R^{108}$, $R^{109}$, $R^{110}$, $R^{111}$, $R^{112}$, $R^{113}$, $R^{114}$, $R^{115}$, $R^{116}$, $R^{117}$, $R^{118}$, $R^{119}$, $R^{120}$, and $R^{121}$ each are independently a hydrogen atom, aliphatic group or aryl group.

Preferred among the foregoing substituents are halogen atom, aliphatic group, aryl group, —$OR^{101}$, —$SR^{102}$, —$NR^{105}R^{106}$, —$SO_2R^{109}$, —$NR^{112}CONR^{113}R^{114}$, —$NR^{115}CO_2R^{116}$ and —$NR^{120}SO_2R^{121}$. Even more desirable among these substituents are halogen atom, aliphatic group, aryl group, —$OR^{101}$, —$SR^{102}$, —$NR^{105}R^{106}$ and —$SO_2R^{109}$. Still even more desirable among these substituents are halogen atom, alkyl group, aryl group, alkoxy group, phenoxy group, and dialkylamino group. Still even more desirable among these substituents are halogen atom, $C_{1-10}$ alkyl group, $C_{6-10}$ aryl group, and $C_{1-10}$ alkoxy group. Most desirable among these substituents are halogen atom, and $C_{1-4}$ alkyl group.

The term "aliphatic group" as used herein is meant to indicate an alkyl, alkenyl, alkinyl or aralkyl group.

A preferred example of the 5- or 6-membered ring formed by $Z^{11}$ and $Z^{12}$ is an aromatic ring or heterocyclic aromatic group. Examples of such an aromatic ring or heterocyclic aromatic group include furan ring, thiophene ring, imidazole ring, thiazole ring, oxazole ring, pyrrole ring, pyrazole ring, 1,2,3-triazole ring, 1,2,4-triazole ring, selenazole ring, oxadiazole ring, thiadiazole ring, benzene ring, pyridine ring, pyrimidine ring, pyrazine ring, and pyridazine ring. $Z^{11}$ is preferably a thiophene ring, imidazole ring, thiazole ring, oxazole ring, pyrrole ring, pyrazole ring, benzene ring or pyridine ring, more preferably a thiazole ring, pyrrole ring, benzene ring or pyridine ring, most preferably benzene ring, among the foregoing rings. $Z^{12}$ is preferably an imidazole ring, thiazole ring, oxazole ring, pyrrole ring, pyrazole ring, 1,2,3-triazole ring, 1,2,4-triazole ring, pyridine ring or pyrimidine ring, more preferably an imidazole ring, thiazole ring, pyrrole ring, pyrazole ring, pyridine ring or pyrimidine ring, even more preferably pyrazole ring or pyridine ring, among the foregoing rings. The number of carbon atoms in $Z^{11}$ and $Z^{12}$ are each preferably from 3 to 40, more preferably from 3 to 30, particularly from 3 to 20.

$Ln^1$ represents a divalent group. Examples of the divalent group represented by $Ln^1$ include —$C(R^{131})(R^{132})$—, —$N(R^{133})$—, —O—, —$P(R^{134})$—, and —S—. $R^{131}$ and $R^{132}$ each independently represent a hydrogen atom, halogen atom, aliphatic group, aryl group, heterocyclic group, cyano group, —$OR^{141}$, —$SR^{142}$, —$CO_2R^{143}$, —$OCOR^{144}$, —NR$^{145}$R$^{146}$, —CONR$^{147}$R$^{148}$, —SO$_2$R$^{149}$, —SO$_2$NR$^{150}$R$^{151}$, —NR$^{152}$CONR$^{153}$R$^{154}$, —NR$^{155}$CO$_2$R$^{156}$, —COR$^{157}$, —NR$^{158}$COR$^{159}$ or —NR$^{160}$SO$_2$R$^{161}$ in which R$^{141}$, R$^{142}$, R$^{143}$, R$^{144}$, R$^{145}$, R$^{146}$, R$^{147}$, R$^{148}$, R$^{149}$, R$^{150}$, R$^{151}$, R$^{152}$, R$^{153}$, R$^{154}$, R$^{155}$, R$^{156}$, R$^{157}$, R$^{158}$, R$^{159}$, R$^{160}$, and R$^{161}$ each independently represent a hydrogen atom, aliphatic group or aryl group. R$^{133}$ represents an aliphatic group, aryl group or heterocyclic group. R$^{134}$ represents an aliphatic group, aryl group, heterocyclic group or —OR$^{171}$ in which R$^{171}$ represents a hydrogen atom, aliphatic group or aryl group.

Ln$^1$ is preferably —C(R$^{131}$)(R$^{132}$)—, —O— or —S—, more preferably —C(R$^{131}$)(R$^{132}$)— in which R$^{131}$ and R$^{132}$ each are a hydrogen atom, aliphatic group or aryl group, even more preferably —C(R$^{131}$)(R$^{132}$)— in which R$^{131}$ and R$^{132}$ each are a hydrogen atom or C$_{1-4}$ alkyl group. The number of carbon atoms in is preferably from 0 to 20, more preferably from 0 to 15, particularly from 0 to 10.

Y$^1$ represents a nitrogen atom or carbon atom. When Y$^1$ is a nitrogen atom, b$^1$ represents a single bond. When Y$^1$ is a carbon atom, b$^1$ represents a double bond.

In the formula (7), Z$^{21}$ and Z$^{22}$ each represent a nonmetallic atom group required to form a 5- or 6-membered ring which may have a substituent or may further form a condensed ring with the other ring. Examples of the substituents include halogen atom, aliphatic group, aryl group, heterocyclic group, cyano, nitro, —OR$^{201}$, —SR$^{202}$, —CO$_2$R$^{203}$, —OCOR$^{204}$, —NR$^{205}$R$^{205}$R$^{206}$, —CONR$^{207}$R$^{208}$, —SO$_2$R$^{209}$, —SO$_2$NR$^{210}$R$^{211}$, —NR$^{212}$CONR$^{213}$R$^{214}$, —NR$^{215}$CO$_2$R$^{216}$, —COR$^{217}$, —NR$^{218}$COR$^{219}$, and —NR$^{220}$SO$_2$R$^{221}$ in which R$^{201}$, R$^{202}$, R$^{203}$, R$^{204}$, R$^{205}$, R$^{206}$, R$^{207}$, R$^{208}$, R$^{209}$, R$^{210}$, R$^{211}$, R$^{212}$, R$^{213}$, R$^{214}$, R$^{215}$, R$^{216}$, R$^{217}$, R$^{218}$, R$^{219}$, R$^{220}$, and R$^{221}$ each are independently a hydrogen atom, aliphatic group or aryl group.

Preferred examples of the substituents on Z$^{21}$ and Z$^{22}$ are the same as that of Z$^{11}$ and Z$^{12}$.

Examples of the 5- or 6-membered ring formed by Z$^{21}$ include furan ring, thiophene ring, imidazole ring, thiazole ring, oxazole ring, pyrrole ring, pyrazole ring, 1,2,3-triazole ring, 1,2,4-triazole ring, selenazole ring, oxanediazole ring, thiadiazole ring, benzene ring, pyridine ring, pyrimidine ring, pyrazine ring, and pyridazine ring. Preferred among these rings are thiophene ring, imidazole ring, thiazole ring, oxazole ring, pyrrole ring, pyrazole ring, benzene ring, and pyridine ring. Even more desirable among these rings are thiazole ring, pyrrole ring, benzene ring, and pyridine ring. Most desirable among these rings is benzene ring. Examples of Z$^{22}$ include pyrazole ring, 1,2,3-triazole ring, 1,2,4-triazole ring, and pyridazine ring. Most desirable among these rings is pyrazole ring. The number of carbon atoms in Z$^{11}$ and Z$^{12}$ are each preferably from 3 to 40, more preferably from 3 to 30, particularly from 3 to 20.

Y$^2$ represents a nitrogen atom or carbon atom. When Y$^2$ is a nitrogen atom, b$^2$ represents a single bond. When Y$^2$ is a carbon atom, b$^2$ represents a double bond.

In the formula (8), X$^{201}$, X$^{202}$, X$^{203}$ and X$^{204}$ each represent a nitrogen atom or C—R and forms a nitrogen-containing heteroaryl 6-membered ring with —C=N—, with the proviso that at least one of X$^{201}$, X$^{202}$, X$^{203}$ and X$^{204}$ represents a nitrogen atom. The nitrogen-containing heteroaryl 6-membered ring formed by X$^{201}$, X$^{202}$, X$^{203}$ or X$^{204}$ with —C=N— may form a condensed ring. R represents a hydrogen atom or substituent. The substituents are as defined with reference to R$^1$ and R$^2$. Preferred examples of the substituents include pyrazine, pyrimidine, pyridazine, triazine, quinoxaline, quinazoline, phthalazine, cinnoline, purine, and pteridine. Even more desirable among these substituents are pyra-zine, pyrimidine, pyridazine, quinoxaline, quinazoline, phthalazine, and cinnoline. Z$^{201}$ represents an atomic group for forming an aryl or heteroaryl ring. The aryl ring formed by Z$^{201}$ is an aryl ring preferably having from 6 to 30 carbon atoms, more preferably from 6 to 20 carbon atoms, particularly from 6 to 12 carbon atoms, e.g., phenyl group, naphthyl group, anthryl group, phenanthryl group, pyrenyl group. The aryl group may further form a condensed ring with carbon rings or heterocycles. The heteroaryl ring represented by Z$^{201}$ is preferably a heteroaryl ring formed by carbon, nitrogen, oxygen and sulfur atoms, more preferably a 5- or 6-membered heteroaryl ring. The heteroaryl ring may further form a condensed ring. The heteroaryl ring preferably has from 2 to 30 carbon atoms, more preferably from 2 to 20 carbon atoms, particularly from 2 to 10 carbon atoms. Examples of the heteroaryl ring represented by Z$^{201}$ include pyridine, pyrimidine, pyrazine, pyridazine, quinoline, isoquinoline, quinoxaline, phthalazine, quinazoline, naphtholidine, cinnoline, pyrimidine, phenanthroline, pyrrole, imidazole, pyrazole, oxazole, oxadiazole, triazole, thiadiazole, benzimidazole, benzoxazole, phenanthridine, chenyl, and furyl. The ring formed by Z$^{201}$ is preferably an aryl ring.

In the formula (9), Z$^{201}$ is as defined in the formula (8). Z$^{301}$ represents anatomic group for forming an aryl or heteroaryl ring condensed to pyridine ring. The aryl ring or heteroaryl ring formed by Z$^{301}$ has the same meaning as that formed by Z$^{201}$ in the formula (8). The ring formed by Z$^{301}$ is preferably an aryl ring.

In the formula (10), Z$^{201}$ is as defined in the formula (8). Z$^{401}$ represents an atomic group which forms an aryl or heteroaryl ring condensed to pyridine ring. The aryl or heteroaryl ring formed by Z$^{401}$ has the same meaning as that formed by Z$^{201}$ in the formula (8). The ring formed by Z$^{401}$ is preferably an aryl ring.

An even more desirable embodiment of the compound of the invention is a compound represented by any one of the following formulae (11) to (20). Particularly preferred among the compounds represented by the formulae (11) to (20) are those represented by the formulae (11), (12) and (14) to (20).

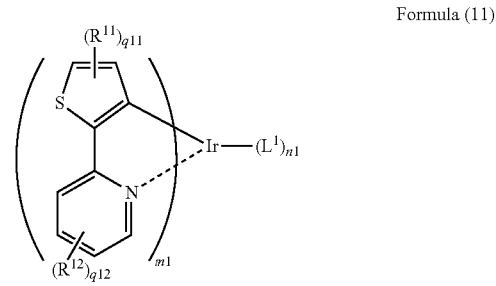

Formula (11)

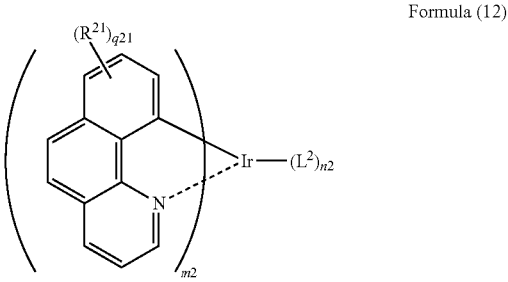

Formula (12)

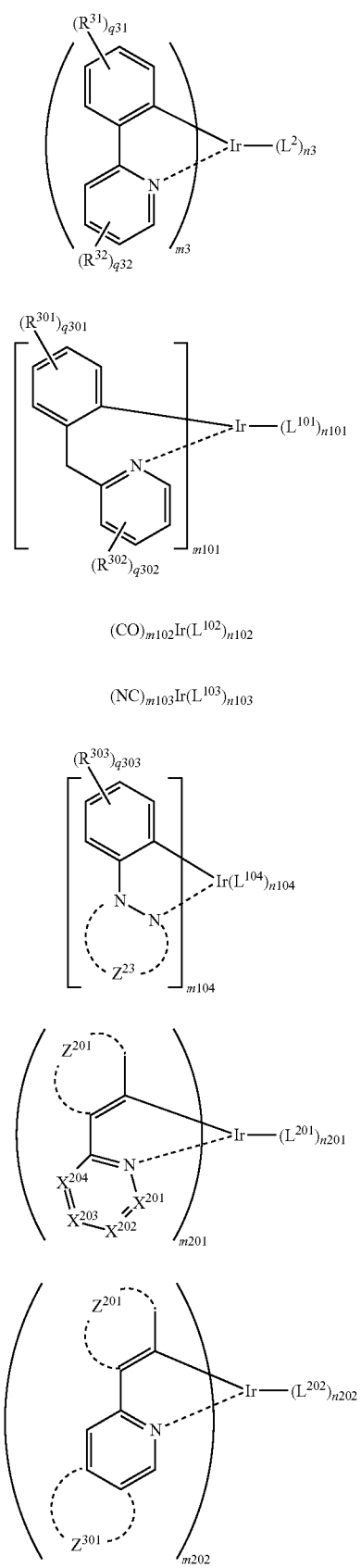

Formula (13)

Formula (14)

Formula (15)

Formula (16)

Formula (17)

Formula (18)

Formula (19)

Formula (20)

The formula (11) will be further described hereinafter. $R^{11}$ and $R^{12}$ each represent a substituent. Examples of the substituent represented by $R^{11}$ or $R^{12}$ include those described with reference to $R^1$ above.

$R^{11}$ and $R^{12}$ each are preferably an alkyl or aryl group, more preferably an alkyl group.

The suffix $q^{11}$ represents an integer of from 0 to 2, preferably 0 or 1, more preferably 0. The suffix $q^{12}$ represents an integer of from 0 to 4, preferably 0 or 1, more preferably 0. When $q^{11}$ and $q^{12}$ each are 2 or more, the plurality of $R^{11}$'s and $R^{12}$'s may be the same or different or may be connected to each other to form a condensed-ring.

$L^1$ represents a ligand. Examples of such a ligand include ligands required to form the foregoing orthometalated iridium complexes and ligands described with reference to other ligands. $L^1$ is preferably a ligand required to form an orthometalated iridium complex, nitrogen-containing heterocyclic ligand, diketone ligand or halogen ligand, more preferably ligand required to form an orthometalated iridium complex or bipyridyl ligand.

The suffix $n^1$ represents an integer of from 0 to 5, preferably 0. The suffix $m^1$ represents an integer of from 1 to 3, preferably 3. The combination of $n^1$ and $m^1$ is preferably such that the metal complex represented by the formula (4) is a neutral complex.

The formula (12) will be further described hereinafter. $R^{21}$, $n^2$, $m^2$, and $L^2$ have the same meaning as $n^1$, $m^1$, and $L^1$, respectively. The suffix $q^{21}$ represents an integer of from 0 to 8, preferably 0. When $q^{21}$ is 2 or more, the plurality of $R^{21}$'s may be the same or different or may be connected to each other to form a condensed ring.

The formula (13) will be further described hereinafter. $R^{31}$, $R^{32}$, $q^{31}$, $q^{32}$, $n^3$, $m^3$, and $L^3$ have the same meaning as $R^1$, $R^2$, $q^1$, $q^2$, $n^1$, $m^1$, and $L^1$, respectively.

The formula (14) will be further described hereinafter. $R^{301}$ and $R^{302}$ each represent a substituent. The substituents represented by $R^{301}$ and $R^{302}$ have the same meaning as those described with reference to $Z^{11}$ and Z. The suffixes $q^{301}$ and $q^{302}$ each represent an integer of from 0 to 4. When $q^{301}$ and $q^{302}$ each represent an integer of from 2 to 4, the plurality of $R^{301}$'s and $R^{302}$'s may be the same or different. The suffixes $q^{301}$ and $q^{302}$ each are preferably 0, 1 or 2, more preferably 0 or 1. The suffixes $m^{101}$ and $n^{101}$ and $L^{101}$ have the same meaning as the suffixes $m^1$ and $n^1$ and $L^1$, respectively.

The formula (15) will be further described hereinafter. $L^{102}$ has the same meaning as $L^1$. The suffix $n^{102}$ represents an integer of from 0 to 5, preferably from 1 to 5. The suffix $m^{102}$ represents an integer of from 1 to 6, preferably from 1 or 2. The combination of $n^{102}$ and $m^{102}$ is preferably such that the metal complex represented by the formula (15) is a neutral complex.

The formula (16) will be further described hereinafter. $L^{103}$, $n^{103}$, and $m^{103}$ have the same meaning as $L^1$, $n^{102}$, and $m^{102}$, respectively.

The formula (17) will be further described hereinafter. $R^{303}$ represents a substituent. The substituent represented by $R^{303}$ has the same meaning as that described with reference to $Z^{21}$, $Z^{23}$, $q^{303}$, $L^{104}$ $n^{104}$ and $m^{104}$ have the same meaning as $Z^{22}$, $q^{301}$, $L^1$, $n^{101}$, and $m^{101}$, respectively.

The formula (18) will be further described hereinafter. In the formula (18), the ring formed by $X^{201}$, $X^{202}$, $X^{203}$ and $X^{204}$ with —C=N and its preferred examples are as defined in the formula (8). $Z^{201}$ represents an atomic group required to form an aryl or heteroaryl ring as defined in the formula (8). Preferred examples of $Z^{201}$, too, are as defined in the formula (8). The suffixes $n^{201}$ and $m^{201}$ and $L^{201}$ have the same meaning as the suffixes $n^1$ and $m^1$ and $L^1$, respectively.

In the formula (19), $Z^{201}$ and $Z^{301}$ and their preferred examples are as defined in the formula (9). The suffixes $n^{202}$ and $m^{202}$ and $L^{202}$ have the same meaning as the suffixes $n^1$ and $m^1$ and $L^1$, respectively.

In the formula (20), $Z^{201}$ and $Z^{401}$ and their preferred examples are as defined in the formula (10). The suffixes $n^{203}$ and $m^{203}$ and $L^{203}$ have the same meaning as the suffixes $n^1$ and $m^1$ and $L^1$ respectively.

The compound of the invention may be a so-called low molecular compound having one repeating unit such as one represented by the formula (1) or may be a so-called oligomer or polymer compound having a plurality of repeating units such as one represented by the formula (1) (having a weight-average molecular weight (in polystyrene equivalence) of preferably from 1,000 to 5,000,000, more preferably from 2,000 to 1,000,000, even more preferably from 3,000 to 100,000). The compound of the invention is preferably a low molecular compound.

Examples of the compound to be used in the invention will be given below, but the present invention should not be construed as being limited thereto.

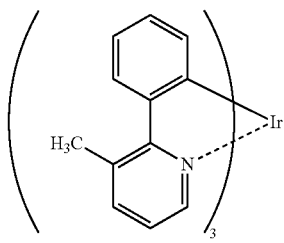
(1-1)

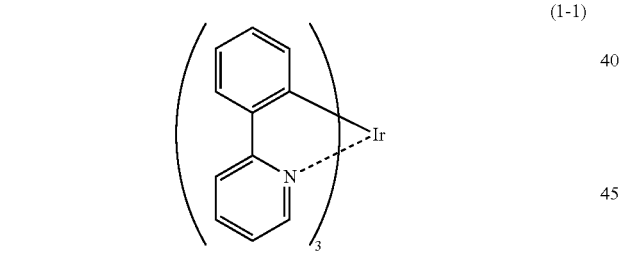
(1-2)

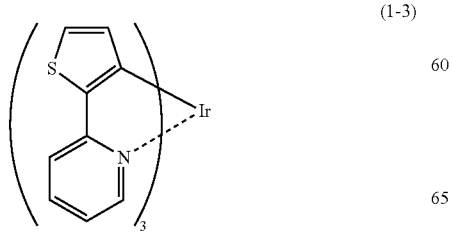
(1-3)

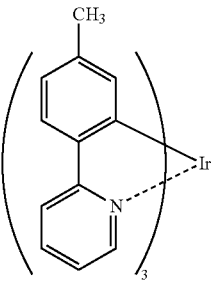
(1-4)

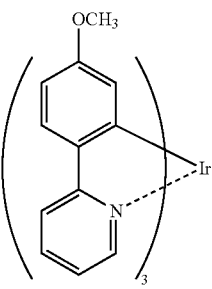
(1-5)

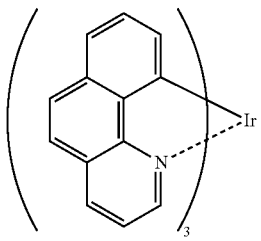
(1-6)

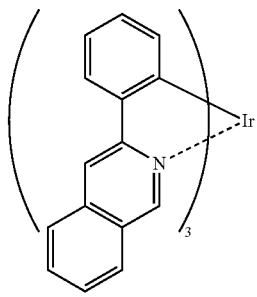
(1-7)

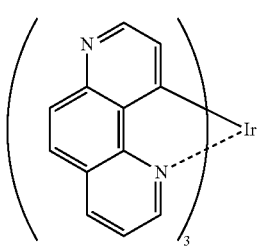
(1-8)

(1-9)

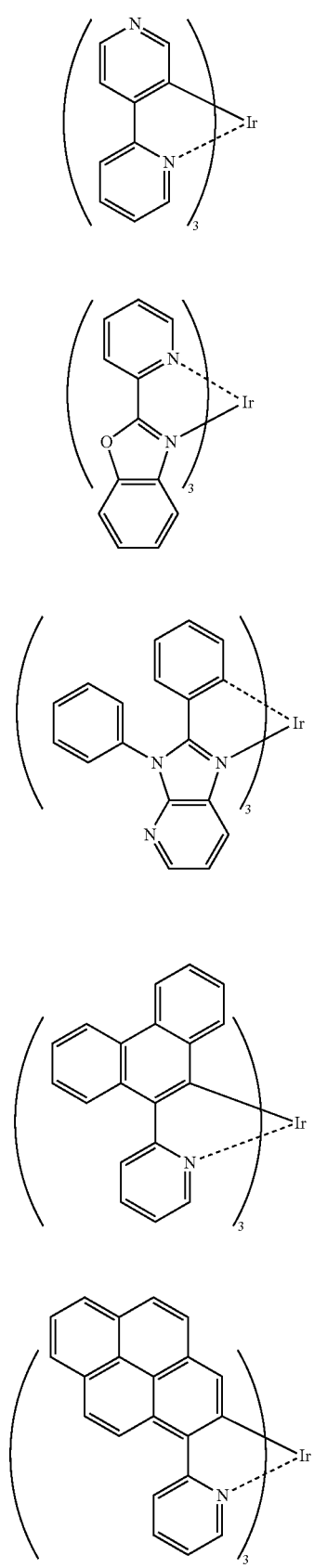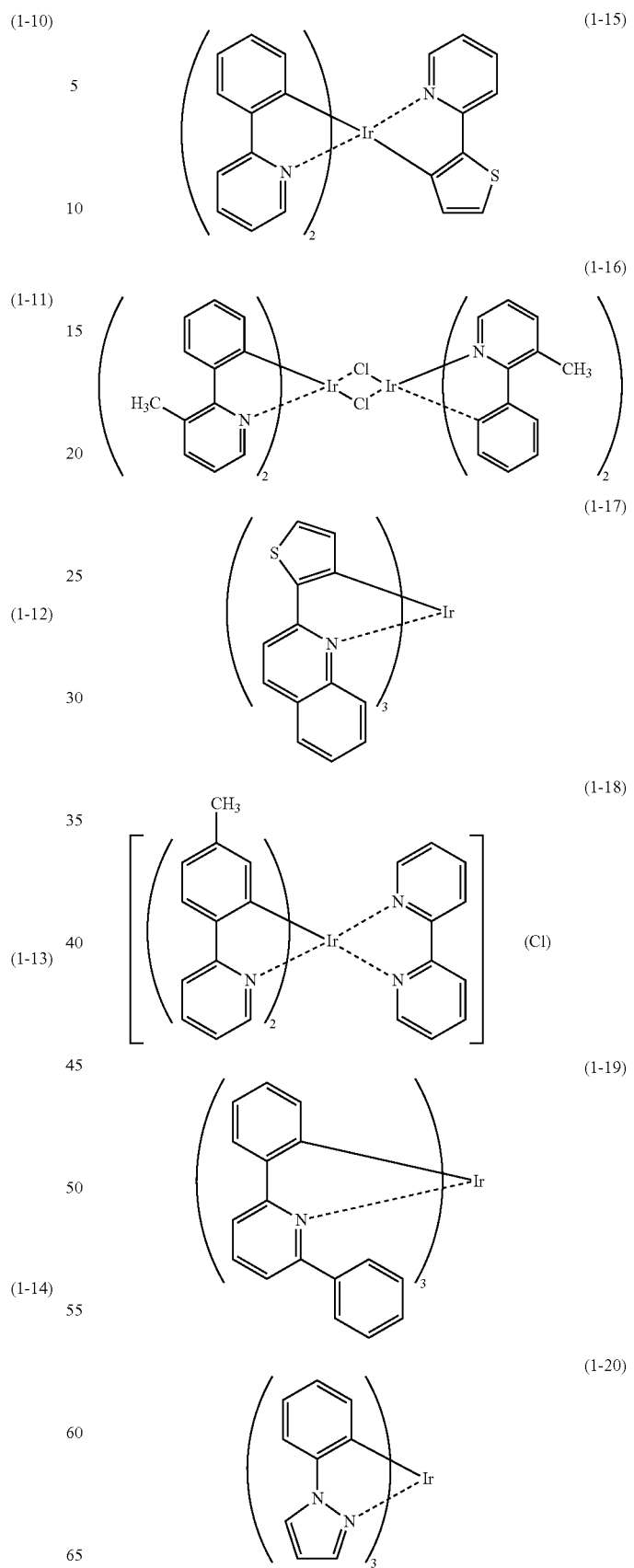

(1-21)
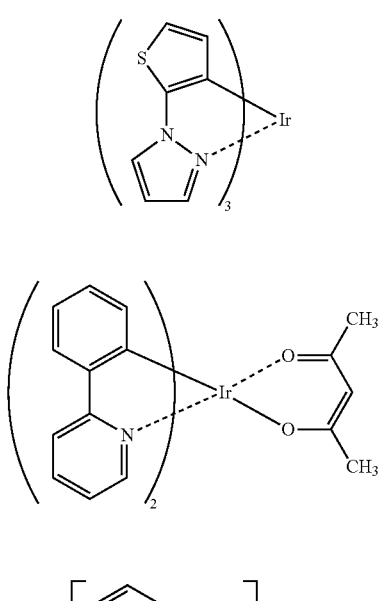
(1-22)
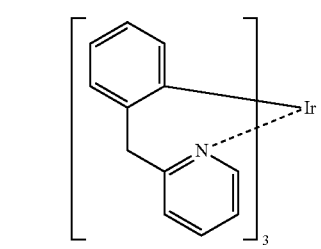
(1-23)
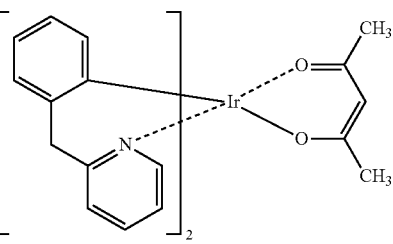
(1-24)
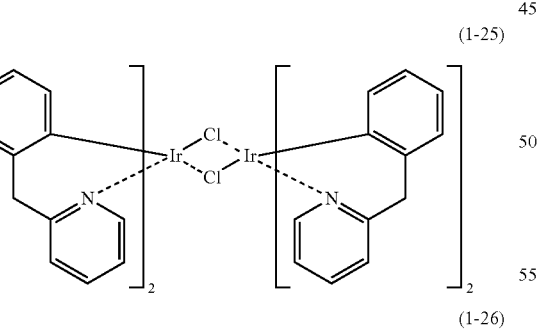
(1-25)
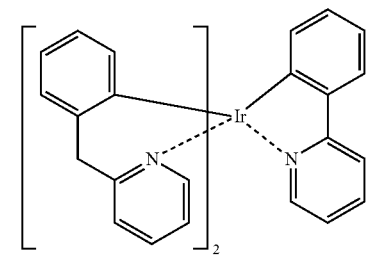
(1-26)
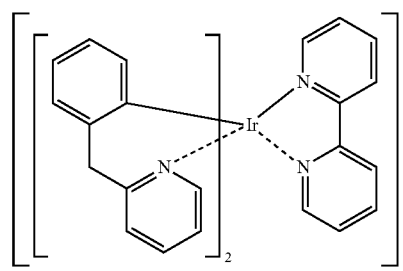
(1-27)
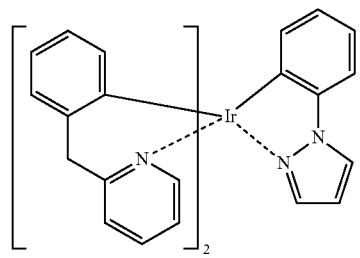
(1-28)
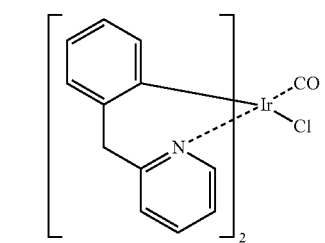
(1-29)
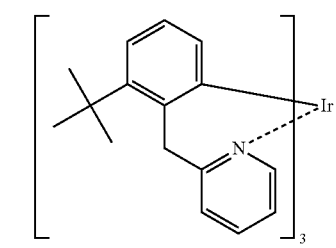
(1-30)
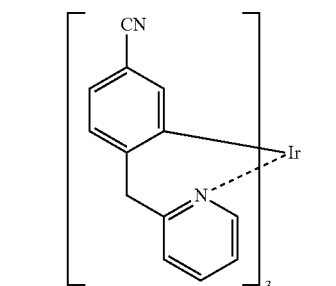
(1-31)
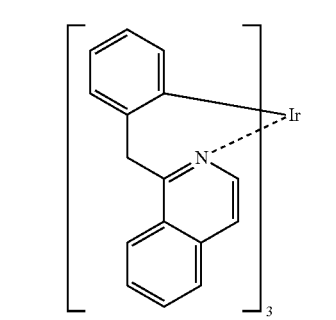
(1-32)

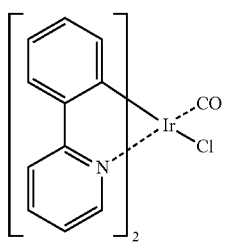
(1-33)
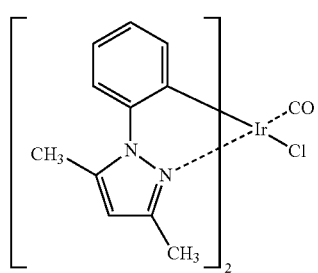
(1-34)
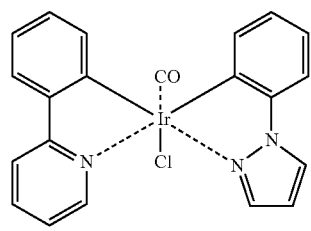
(1-35)
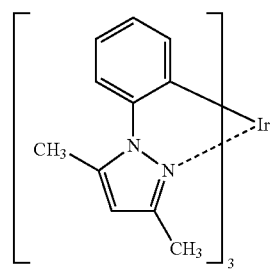
(1-36)
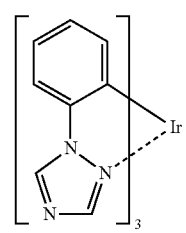
(1-37)
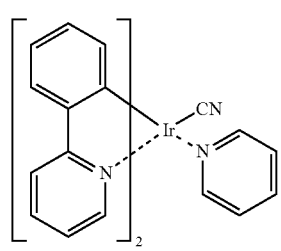
(1-38)
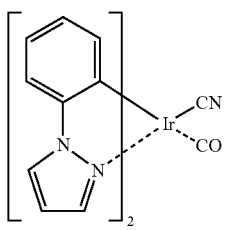
(1-39)
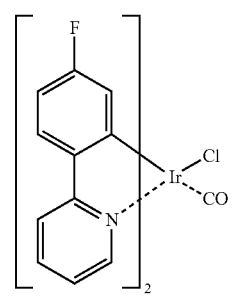
(1-40)
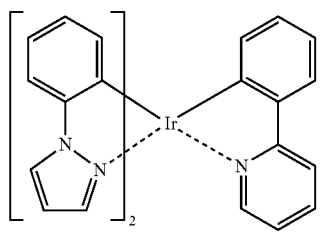
(1-41)
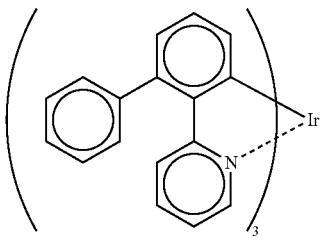
(1-42)
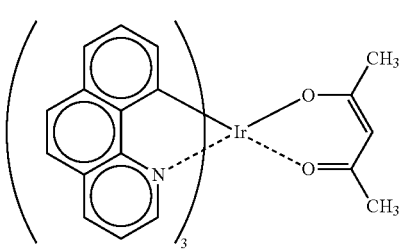
(1-43)
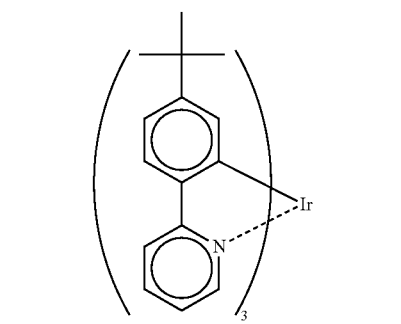
(1-44)

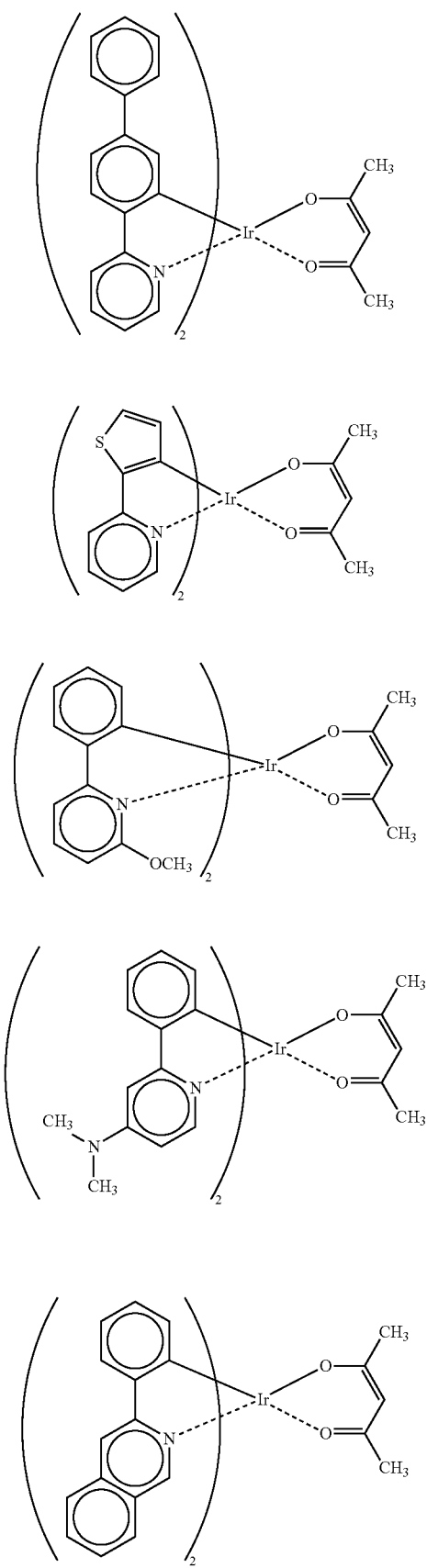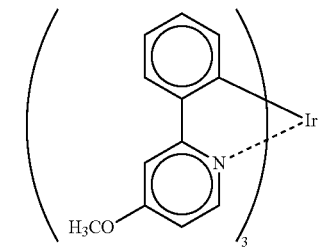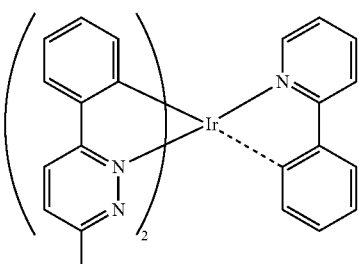

(1-56)
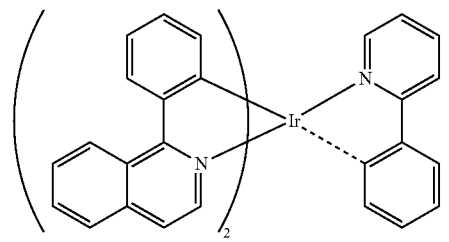
(1-57)
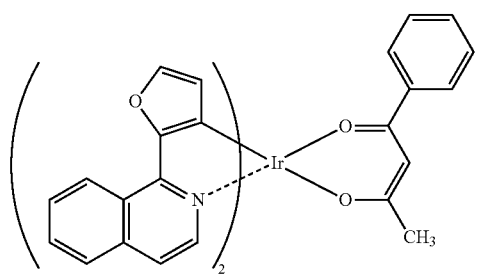
(1-58)
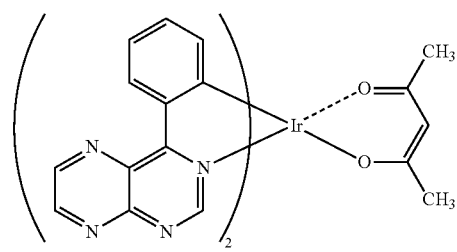
(1-59)
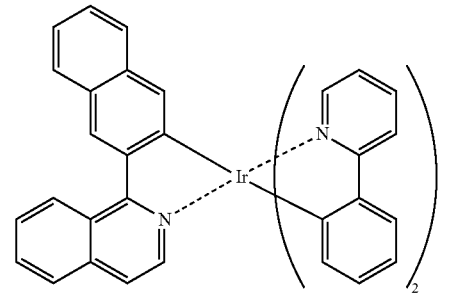
(1-60)
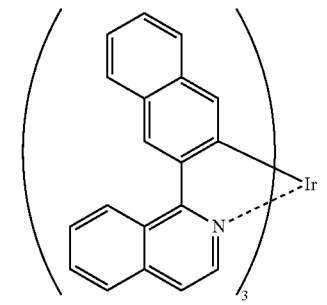
(1-61)
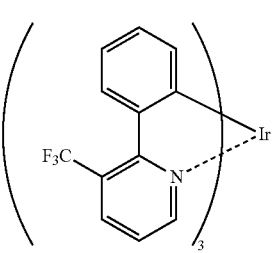
(1-62)
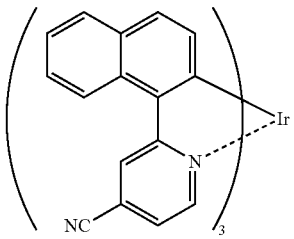
(1-63)
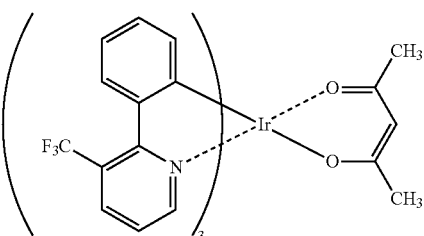
(1-64)
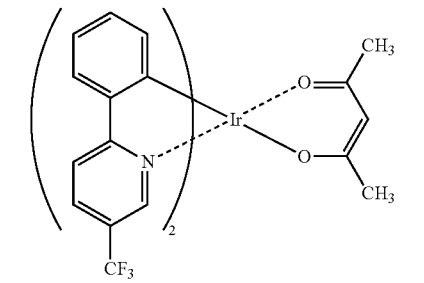
(1-65)
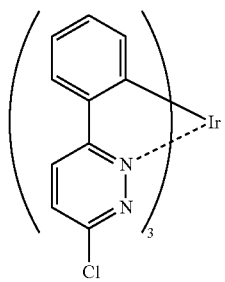
(1-66)
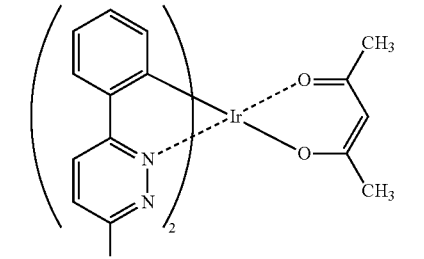
(1-67)
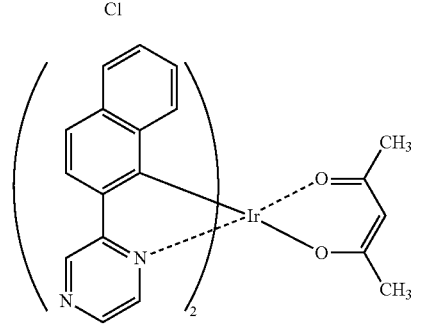

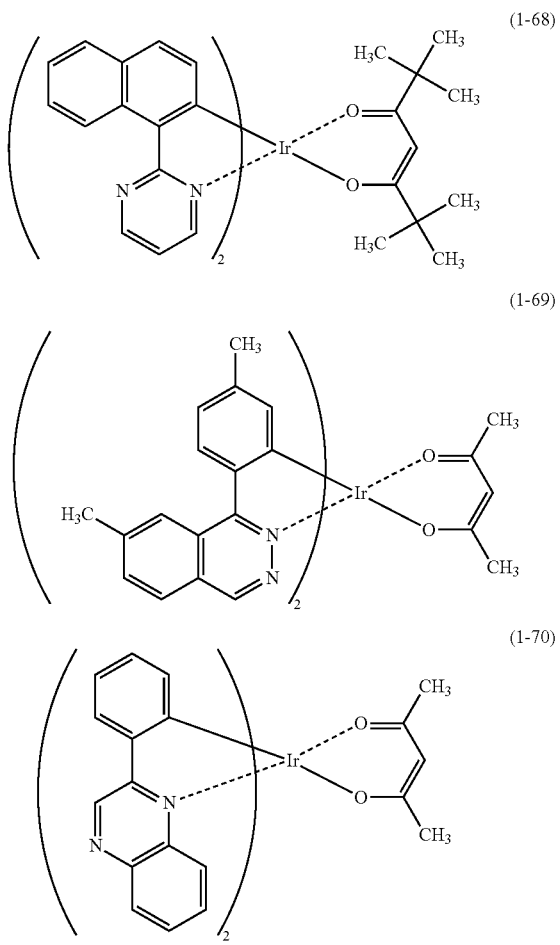

The synthesis of the compound of the invention can be accomplished by any known method as disclosed in "Inorg. Chem.", No. 30, page 1,685, 1991, No. 27, page 3,464, 1988, No. 33, page 545, 1994, "Inorg. Chem. Acta.", No. 181, page 245, 1991, "J. Organomet. Chem.", No. 35, page 293, 1987, "J. Am. Chem. Soc.", No. 107, page 1,431, 1985, etc.

Some examples of synthesis of the compound of the invention will be described below.

As mentioned below, hexahalogenated iridium (III) compound and hexahalogenated iridium (IV) compound can be used as starting materials to synthesize the compound of the invention.

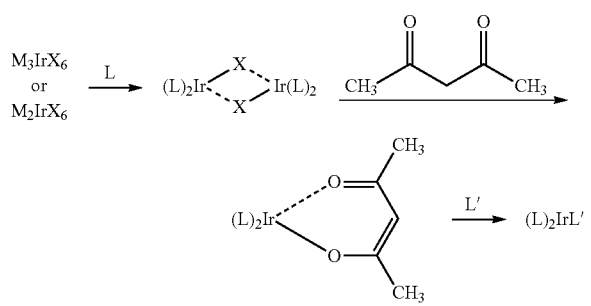

SYNTHESIS EXAMPLE 1

Synthesis of Exemplary Compound (1-25)

Into a three neck distillation flask were charged 5.22 g of $K_3IrCl_6$, 16.9 g of 2-benzylpyridine and 50 ml of glycerol. The contents of the flask were then heated to an internal temperature of 200° C. with stirring in an argon atmosphere for 1 hour. Thereafter, the contents of the flask were cooled to an internal temperature of 40° C. To the material was then added 150 ml of methanol. The material was further stirred for 1 hour, and then subjected to filtration with suction to obtain a crystal which was then purified through silica gel column chromatography to obtain 4.34 g of the desired exemplary compound (1-25) (yield: 77%).

SYNTHESIS EXAMPLE 2

Synthesis of Exemplary Compound (1-24)

Into a three neck distillation flask were charged 5.64 g of the exemplary compound (1-25), 560 ml of chloroform and 10.0 g of acetylacetone. To the contents was then added dropwise 20.1 ml of a 28% methanol solution of sodium methylate at room temperature with stirring in 20 minutes. After the termination of dropwise addition, the mixture was then stirred at room temperature for 5 hours. The mixture was then extracted with 40 ml of saturated brine and 400 ml of water. The resulting chloroform phase was washed with a mixture of 300 ml of saturated brine and 30 ml of water four times, dried over anhydrous sodium sulfate, and then concentrated through a rotary evaporator. The resulting residue was then purified through silica gel column chromatography to obtain 5.59 g of the desired exemplary compound (1-24) (yield: 89%).

SYNTHESIS EXAMPLE 3

Synthesis of Exemplary Compound (1-26)

Into a three neck distillation flask were charged 6.28 g of the exemplary compound (1-24), 15.5 g of 2-phenylpyridine and 63 ml of glycerol. The contents of the flask were then heated to an internal temperature of 170° C. with stirring in an argon atmosphere for 15 minutes. Thereafter, the contents of the flask were cooled to an internal temperature of 40° C. The mixture was then extracted with 500 ml of chloroform, 40 ml of saturated brine and 400 ml of water. The resulting chloroform phase was washed with a mixture of 40 ml of saturated brine and 400 ml of water four times, and then dried over anhydrous sodium sulfate. The material was then concentrated through a rotary evaporator. The resulting residue was then purified through silica gel column chromatography to obtain 5.60 g of the desired exemplary compound (1-26) (yield: 82%).

SYNTHESIS EXAMPLE 4

Synthesis of Exemplary Compound (1-29)

Into a three neck distillation flask were charged 5.64 g of the exemplary compound (1-25) and 560 ml of chloroform. Into the contents of the flask was blown carbon monoxide with stirring over an ice bath for 10 minutes. The mixture was further stirred for 1 hour. The mixture was then extracted with 40 ml of saturated brine and 400 ml of water. The resulting chloroform phase was washed with a mixture of 300 ml of saturated brine and 30 ml of water four times, dried over anhydrous sodium sulfate, and then concentrated through a rotary evaporator. The resulting residue was then purified through silica gel column chromatography to obtain 4.38 g of the desired exemplary compound (1-29) (yield: 74%).

SYNTHESIS EXAMPLE 5

Synthesis of Exemplary Compounds (1-65) and (1-66)

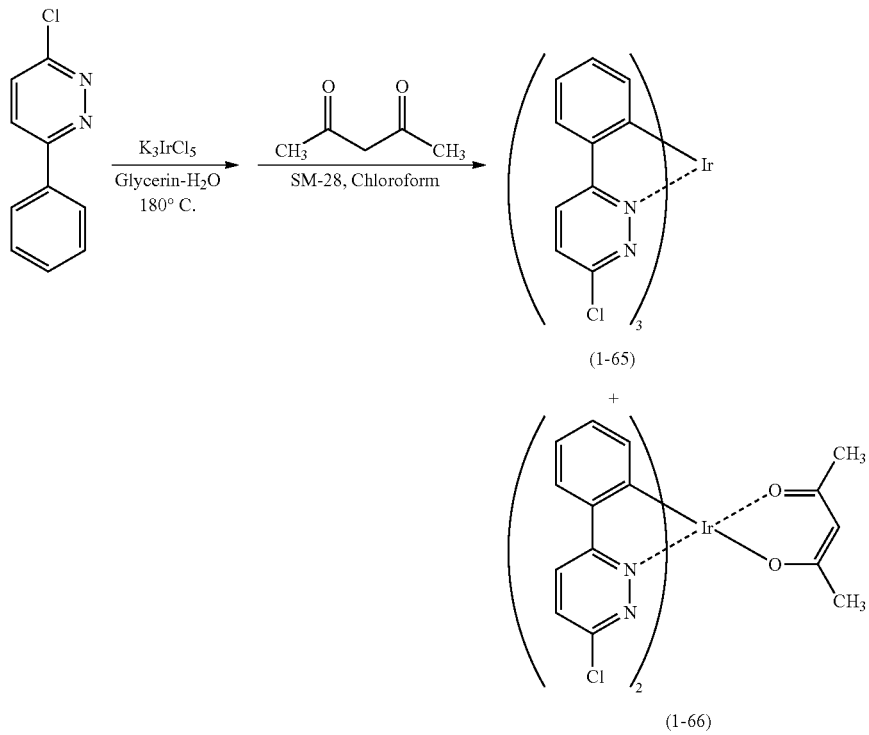

(1-65)

+

(1-66)

To a solution of 1.35 g of $K_3IrCl_6$ in 25 ml of water were then added 1.01 g of 3-chloro-6-phenylpyridazine and 100 ml of glycerin. The mixture was heated to a temperature of 180° C. with stirring for 4 hours. After the termination of reaction, the reaction solution was then allowed to cool. To the reaction solution was then added water. The resulting dark brown solid was withdrawn by filtration, and then dried. To a solution of the resulting solid in 1 l of chloroform were then added 2.5 g of acetylacetone and 4.8 g of a 28% methanol solution of sodium methoxide. The reaction mixture was heated under reflux so that it was reacted for 2 hours. After the termination of reaction, the reaction solution was then poured into 500 ml of water. The reaction solution was then extracted with chloroform. The extract was dried over anhydrous magnesium sulfate, and then concentrated. The resulting solid was then developed through silica gel column chromatography. An orange-colored fraction which had been first eluted was concentrated, recrystallized from a mixture of chloroform and ethanol, and then dried to obtain 66 mg of the desired exemplary compound 1-65. The compound thus obtained was then measured for solution fluorescent spectrum. As a result, the fluorescence was found to have λmax of 578 nm ($CHCl_3$). A reddish orange-colored fraction which had been subsequently eluted was concentrated, recrystallized from a mixture of chloroform and ethanol, and then dried to obtain 294 mg of the desired exemplary compound I-66. The compound thus obtained was then measured for solution fluorescent spectrum. As a result, the fluorescence was found to have λmax of 625 nm ($CHCl_3$).

The second embodiment of the present invention will be further described hereinafter.

The light-emitting device is an organic light-emitting device having an external quantum efficiency of 5% or more and λmax of 590 nm or more. The organic light-emitting device to be used herein is not specifically limited. In practice, however, an organic EL (electroluminescence) device.

The external quantum efficiency of the light-emitting device of the invention is preferably 7% or more, more preferably 90 or more, even more preferably 11% or more, particularly 13% or more.

The light-emitting device of the invention emits light having λmax of preferably 593 nm or more, more preferably 596 nm or more, even more preferably 599 nm or more from the standpoint of purity of red color.

The light-emitting device of the invention is preferably an device comprising a transition metal complex (preferably orthometalated complex), more preferably an iridium complex or platinum complex, even more preferably an orthometalated iridium complex, particularly a compound having a partial structure represented by the following formula (21) or (22).

"orthometalated metal complex" is a generic term for a group of compounds as described in Akio Yamamoto, "Yuki Kinzoku Kagaku-Kiso to Oyo—(Organic Metal Chemistry—Fundamentals and Application)", Shokabosha, pp. 150, 232, 1982, H. Yersin, "Photochemistry and Photophysics of Coordination Compounds", Springer-Verlag, pp. 1-77, pp. 135-146, 1987, etc.

The light-emitting device of the invention preferably comprises a layer comprising a compound having an ionization potential of 5.9 eV or more (more preferably 6.0 eV or more), more preferably an electron-transporting layer having an ionization potential of 5.9 eV or more, provided interposed between the cathode and the light-emitting layer.

The CIE chromaticity value x of light emitted from the light-emitting device of the invention is preferably 0.50 or more, more preferably 0.53 or more, even more preferably 0.57 or more, particularly 0.60 or more from the standpoint of purity of red color.

The CIE chromaticity value y of light emitted from the light-emitting device of the invention is preferably 0.50 or less, more preferably 0.45 or less, even more preferably 0.39 or less.

The half width of spectrum of emission from the light-emitting device of the invention is preferably 100 nm or less, more preferably 90 nm or less, even more preferably 80 nm or less, particularly 70 nm or less from the standpoint of purity of red color.

The compound having a partial structure represented by the formula (21) or (22) will be further described hereinafter.

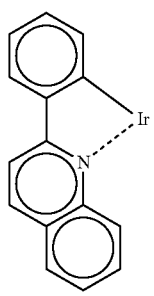

Formula (1)

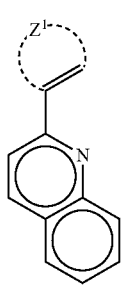

Formula (2)

In the formula (22), $Z^1$ represents an atomic group which forms a heteroaryl ring. The heteroaryl ring represented by $Z^1$ is preferably a heteroaryl ring comprising carbon, nitrogen, oxygen and sulfur atoms, more preferably a 5- or 6-membered heteroaryl ring. The heteroaryl ring represented by $Z^1$ may further form a condensed ring. The heteroaryl ring represented by $Z^1$ preferably has from 2 to 30 carbon atoms, more preferably from 2 to 20 carbon atoms, particularly from 2 to 10 carbon atoms. Examples of the heteroaryl ring represented by $Z^1$ include pyridine, pyrimidine, pyrazine, pyridazine, quinoline, isoquinoline, quinoxaline, phthalazine, quinazoline, naphtholidine, cinnoline, pyrimidine, phenanthroline, pyrrole, imidazole, pyrazole, oxazole, oxadiazole, triazole, thiazole, thiadiazole, benzimidazole, benzoxazole, benzthiazole, phenanthridine, thiophene, and furan.

The light-emitting device material defined in Item 16 or 17 has a partial structure represented by the formula (21) or (22). The quinoline ring, phenyl ring and heteroaryl ring represented by the ligand may form a condensed ring and may have a substituent. Examples of these substituents include those described with reference to $R^{11}$ and $R^{12}$ in the formula (23).

The valency of iridium constituting the compound having a partial structure represented by the formula (21) or (22) is not specifically limited but is preferably 3. The foregoing compound may have one iridium atom per molecule or may be a so-called binuclear complex having two or more iridium atoms per molecule. The foregoing compound is preferably one having one iridium atom per molecule. This compound may further contain other metal atoms but preferably is a compound having an iridium complex alone.

The compound having a partial structure represented by the formula (21) or (22) may have various ligands. Examples of the other ligands include various known ligands. Examples of these ligands include those described in H. Yersin, "Photochemistry and Photophysics of Coordination Compounds", Springer-Verlag, 1987, Akio Yamamoto, "Yuki Kinzoku Kagaku-Kiso to Oyo—(Organic Metal Chemistry—Fundamentals and Application)", Shokabosha, 1982, etc. Preferred among these ligands are halogen ligands (preferably chlorine ligand), nitrogen-containing heterocyclic ligands (more preferably aryl group-substituted nitrogen-containing derivative (The aryl group substitutes on the carbon atom adjacent to the nitrogen atom constituting the nitrogen-containing heterocyclic group. Examples of the aryl group include phenyl group, naphthyl group, anthryl group, phenanthryl group, and pyrenyl group. The aryl group may further form a condensed ring with carbon rings or heterocycles. Examples of the nitrogen-containing heterocycle include pyridine, pyrimidine, pyrazine, quinoline, isoquinoline, quinoxaline, phthalazine, quinazoline, naphtholidine, cinnoline, perymidine, phenanthroline, pyrrole, imidazole, pyrazole, oxazole, oxadiazole, triazole, thiadiazole, benzimidazole, benzoxazole, benzthiazole, and phenanthridine), heteroaryl group-substituted, nitrogen-containing heterocyclic derivative (The heteroaryl group substitutes on the carbon atom adjacent to the nitrogen atom constituting the nitrogen-containing heterocyclic group. Examples of the aryl group include the foregoing nitrogen-containing heterocyclic derivative, chenyl group, and furyl group), e.g., as phenylpyridine, benzoquinoline, quinolinol, bipyridyl, phenanthroline), diketone ligand, carboxylic acid ligand, and $PF_6$ ligand. Preferred among these ligands are aryl group-substituted nitrogen-containing heterocyclic derivative, and diketone ligand.

There may be used one or a plurality of kinds of ligands constituting the compound of the invention. The number of ligands in the complex is preferably from 1 to 3, particularly from 1 or 2, more preferably 2.

The compound of the invention may be a neutral complex or ionic complex having a counter salt (e.g., chlorine ion, $PF_6$ ion, $ClO_4$ ion, quaternary salt (e.g., tetrabutyl ammonium)), preferably neutral complex.

The number of carbon atoms in the compound of the invention is preferably from 15 to 100, more preferably from 20 to 70, even more preferably from 30 to 60.

Preferred embodiments of the compound of the invention are compounds represented by the following formulae (23) and (24).

The formula (23) will be described hereinafter.

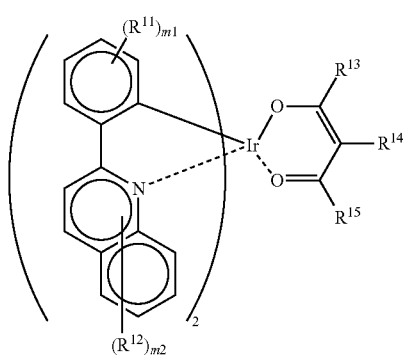

(23)

$R^{11}$ and each represent a substituent. $R^{11}$'s or $R^{12}$'s may be connected to own or each other to form a cyclic structure. Examples of the substituents represented by $R^{11}$ and $R^{12}$ include alkyl group (alkyl group preferably having from 1 to 30, more preferably from 1 to 20, particularly from 1 to 10 carbon atoms, e.g., methyl, ethyl, iso-propyl, tert-butyl, n-octyl, n-decyl, n-hexadecyl, cyclopropyl, cyclopentyl, cyclohexyl, trifluoromethyl, pentafluoroethyl), alkenyl group (alkenyl group preferably having from 2 to 30 carbon atoms, more preferably from 2 to 20 carbon atoms, particularly from 2 to 10 carbon atoms, e.g., vinyl, allyl, 2-butenyl, 3-pentenyl), alkinyl group (alkinyl group preferably having from 2 to 30 carbon atoms, more preferably from 2 to 20 carbon atoms, particularly from 2 to 10 carbon atoms, e.g., propargyl, 3-pentinyl), -aryl group (aryl group preferably having from 6 to 30 carbon atoms, more preferably from 6 to 20 carbon atoms, particularly from 6 to 12 carbon atoms, e.g., phenyl, p-methylphenyl, naphthyl, anthranyl), amino group (amino group preferably having from 0 to 30 carbon atoms, more preferably from 0 to 20 carbon atoms, particularly from 0 to 10 carbon atoms, e.g., amino, methylamino, dimethylamino, diethylamino, dibenzylamino, diphenylamino, ditollylamino), alkoxy group (alkoxy group preferably having from 1 to 30 carbon atoms, more preferably from 1 to 20 carbon atoms, particularly from 1 to 12 carbon atoms, e.g., methoxy, ethoxy, butoxy, 2-ethylhexyloxy), aryloxy group (aryloxy group preferably having from 6 to 30 carbon atoms, more preferably from 6 to 20 carbon atoms, particularly from 6 to 12 carbon atoms, e.g., phenyloxy, 1-naphthyloxy, 2-naphthyloxy), heteroaryloxy group (heteroaryloxy group preferably having from 1 to 30 carbon atoms, more preferably from 1 to 20 carbon atoms, particularly from 1 to 12 carbon atoms, e.g., pyridyloxy, pyrazyloxy, pyrimidyloxy, quinolyloxy), acyl group (acyl group preferably having from 1 to 30 carbon atoms, more preferably from 1 to 20 carbon atoms, particularly from 1 to 12 carbon atoms, e.g., acetyl, benzoyl, formyl, pivaloyl), alkoxycarbonyl group (alkoxycarbonyl group preferably having from 2 to 30 carbon atoms, more preferably from 2 to 20 carbon atoms, particularly from 2 to 12 carbon atoms, e.g., methoxycarbonyl, ethoxycarbonyl), aryloxycarbonyl group (aryloxycarbonyl group preferably having from 7 to 30 carbon atoms, more preferably from 7 to 20 carbon atoms, particularly from 7 to 12 carbon atoms, e.g., phenyloxycarbonyl), acyloxy group (acyloxy group preferably having from 2 to 30 carbon atoms, more preferably from 2 to 20 carbon atoms, particularly from 2 to 10 carbon atoms, e.g., acetoxy, benzoyloxy), acylamino group (acylamino group preferably having from 2 to 30 carbon atoms, more preferably 2 to 20 carbon atoms, particularly from 2 to 10 carbon atoms, e.g., acetylamino, benzoylamino), alkoxycarbonylamino group (alkoxycarbonylamino group preferably having from 2 to 30 carbon atoms, more preferably 2 to 20 carbon atoms, particularly from 2 to 12 carbon atoms, e.g., methoxycarbonylamino), aryloxycarbonylamino group (aryloxycarbonylamino group preferably having from 7 to 30 carbon atoms, more preferably 7 to 20 carbon atoms, particularly from 7 to 12 carbon atoms, e.g., phenyloxycarbonylamino), sulfonylamino group (sulfonylamino group preferably having from 1 to 30 carbon atoms, more preferably 1 to 20 carbon atoms, particularly from 1 to 12 carbon atoms, e.g., methanesulfonylamino, benzenesulfonylamino), sulfamoyl group (sulfamoyl group preferably having from 2 to 30 carbon atoms, more preferably 2 to 20 carbon atoms, particularly from 2 to 10 carbon atoms, e.g., sulfamoyl, methylsulfamoyl, dimethylsulfamoyl, phenylsulfamoyl), carbamoyl group (carbamoyl group preferably having from 1 to 30 carbon atoms, more preferably 1 to 20 carbon atoms, particularly from 1 to 12 carbon atoms, e.g., carbamoyl, methylcarbamoyl, diethylcarbamoyl, phenylcarbamoyl), alkylthio group (alkylthio group preferably having from 1 to 30 carbon atoms, more preferably 1 to 20 carbon atoms, particularly from 1 to 12 carbon atoms, e.g., methylthio, ethylthio), arylthio group (arylthio group preferably having from 6 to 30 carbon atoms, more preferably 6 to 20 carbon atoms, particularly from 6 to 12 carbon atoms, e.g., phenylthio), heteroarylthio group (heteroarylthio group preferably having from 1 to 30 carbon atoms, more preferably 1 to 20 carbon atoms, particularly from 1 to 12 carbon atoms, e.g., pyridylthio, 2-benzimizolylthio, 2-benzoxazoylthio, 2-benzthiazolylthio), sulfonyl group (sulfonyl group preferably having from 1 to 30 carbon atoms, more preferably 1 to 20 carbon atoms, particularly from 1 to 12 carbon atoms, e.g., mesyl, tosyl), sulfinyl group (sulfinyl group preferably having from 1 to 30 carbon atoms, more preferably 1 to 20 carbon atoms, particularly from 1 to 12 carbon atoms, e.g., methanesulfinyl, benzenesulfinyl), ureide group (ureide group preferably having from 1 to 30 carbon atoms, more preferably 1 to 20 carbon atoms, particularly from 1 to 12 carbon atoms, e.g., ureide, methylureide, phenylureide), phosphoric acid amide group (phosphoric acid amide group preferably having from 1 to 30 carbon atoms, more preferably 1 to 20 carbon atoms, particularly from 1 to 12 carbon atoms, e.g., diethylphosphoric acid amide, phenylphosphoric acid amide), hydroxy group, mercapto group, halogen atom (e.g., fluorine atom, chlorine atom, bromine atom, iodine atom), cyano group, sulfo group, carboxyl group, nitro group, hydroxamic acid group, sulfino group, hydrazino group, imino group, heterocyclic group (heterocyclic group preferably having from 1 to 30 carbon atoms, more preferably from 1 to 12 carbon atoms, and containing as hetero atoms nitrogen atom, oxygen atom and sulfur atom, e.g., imidazolyl, pyridyl, quinolyl, furyl, chenyl, piperidyl, morpholino, benzoxazolyl, benzimidazolyl, benzthiazolyl), and silyl group (silyl group preferably having from 3 to 40 carbon atoms, more preferably 3 to 30 carbon atoms, particularly from 3 to 24 carbon atoms, e.g., trimethylsilyl, triphenylsilyl). These substituents may be further substituted. $R^1$'s or $R^2$'s may be connected to each other, or $R^1$ and $R^2$ may be connected to each other to form a condensed ring structure.

Preferred among these groups represented by $R^{11}$ and $R^{12}$ are alkyl group, aryl group, heteroaryl group, alkoxy group, halogen atom, cyano group, and cyclic structure obtained by the connection of $R^{11}$'s or $R^{12}$'s to own or each other. More desirable among these groups are alkyl group, aryl group, and groups which are connected to each other to form an aromatic group. Even more desirable among these groups are alkyl group, and groups which are connected to each other to form an aromatic group.

$R^{13}$, $R^{14}$ and $R^{15}$ each represent a hydrogen atom or substituent. Examples of the substituents represented by $R^{13}$ and $R^{15}$ include alkyl group, alkenyl group, alkinyl group, aryl group, heterocyclic group, and alkoxy group which are the same as those described with reference to $R^{11}$ and $R^{12}$. Preferred among the groups represented by $R^{13}$ and $R^{15}$ are alkyl group, aryl group, and heteroaryl group. More desirable among these groups is alkyl group.

Examples of the substituent represented by $R^{14}$ include alkyl group, alkenyl group, alkinyl group, aryl group, heteroaryl group, heterocyclic group, and cyano group which are the same as those described with reference to $R^{11}$ and $R^{12}$. Preferred among the groups represented by $R^{14}$ are hydrogen atom, and alkyl group. More desirable among these groups is hydrogen atom.

The suffix $m^1$ represents an integer of from 0 to 4. The suffix $m^2$ represents an integer of from 0 to 6. When $m^1$ and $m^2$ are plural, the plurality of $R^{11}$'s and $R^{12}$'s may be the same or different. The $m^1$ is preferably from 0 to 2. The $m^2$ is preferably from 0 to 4, more preferably from 0 to 2.

The formula (24) will be described hereinafter.

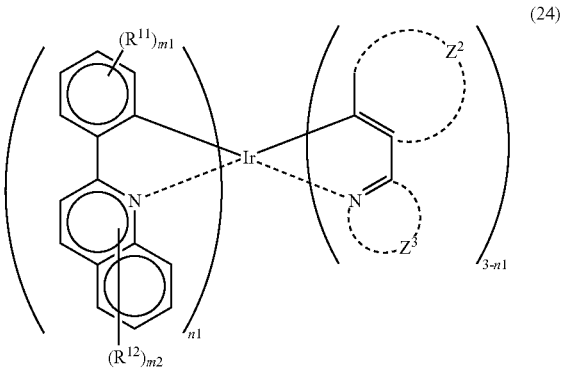

(24)

In the formula (24), $R^{11}$, $R^{12}$, $m^1$, and $m^2$ are as defined in the formula (23). $Z^2$ represents an atomic group which forms an aryl or heteroaryl ring. The aryl ring formed by $Z^2$ preferably has from 6 to 30 carbon atoms, more preferably from 6 to 20 carbon atoms, particularly from 6 to 12 carbon atoms. Examples of the aryl group represented by $Z^2$ include phenyl group, naphthyl group, anthryl group, phenanthryl group, and pyrenyl group. $Z^2$ may further form a condensed ring with carbon rings or heterocycles. The heteroaryl ring represented by $Z^2$ is preferably a heteroaryl ring comprising carbon, nitrogen, oxygen and sulfur atoms, more preferably a 5- or 6-membered heteroaryl ring. The heteroaryl ring represented by $Z^2$ may further form a condensed ring. The heteroaryl ring represented by $Z^2$ preferably has from 2 to 30 carbon atoms, more preferably from 2 to 20 carbon atoms, particularly from 2 to 10 carbon atoms. Examples of the heteroaryl ring represented by $Z^2$ include pyridine, pyrimidine, pyrazine, pyridazine, quinoline, isoquinoline, quinoxaline, phthalazine, quinazoline, naphtholidine, cinnoline, perimidine, phenanthroline, pyrrole, imidazole, pyrazole, oxazole, oxadiazole, triazole, thiadiazole, benzimidazole, benzoxazole, phenanthridine, chenyl, and furyl. The ring formed by $Z^2$ is preferably an aryl ring.

$Z^3$ represents an atomic group which forms a nitrogen-containing heterocycle with —C=N, preferably a nitrogen-containing heteroaryl ring comprising carbon, nitrogen, oxygen and sulfur atoms, more preferably a 5- or 6-membered heteroaryl ring. The nitrogen-containing heteroaryl ring represented by $Z^3$ may further form a condensed ring. The nitrogen-containing heteroaryl ring represented by $Z^3$ preferably has from 2 to 30 carbon atoms, more preferably from 2 to 20 carbon atoms, particularly from 2 to 10 carbon atoms. Examples of the nitrogen-containing heteroaryl ring represented by $Z^3$ include pyridine, pyrimidine, pyrazine, pyridazine, quinoline, isoquinoline, quinoxaline, phthalazine, quinazoline, naphtholidine, cinnoline, perimidine, phenanthroline, pyrrole, imidazole, pyrazole, oxazole, oxadiazole, triazole, thiadiazole, benzimidazole, benzoxazole, benzthiazole, and phenanthridine.

The quinoline derivative ligand in the compound of the formula (21), (22), (23) or (24) is more preferably formed by at least four rings.

The compound of the invention may be a so-called low molecular compound having one repeating unit such as one represented by the formula (21) or (22) or may be a so-called oligomer or polymer compound having a plurality of repeating units such as one represented by the formula (21) or (22) (having a weight-average molecular weight (in polystyrene equivalence) of preferably from 1,000 to 5,000,000, more preferably from 2,000 to 1,000,000, even more preferably from 3,000 to 100,000). The compound of the invention is preferably a low molecular compound.

Examples of the compound of the invention will be given below, but the present invention should not be construed as being limited thereto.

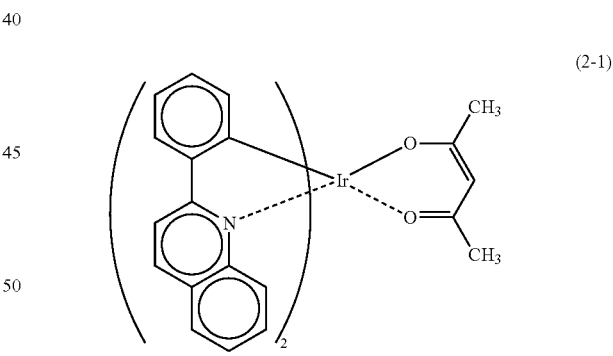

(2-1)

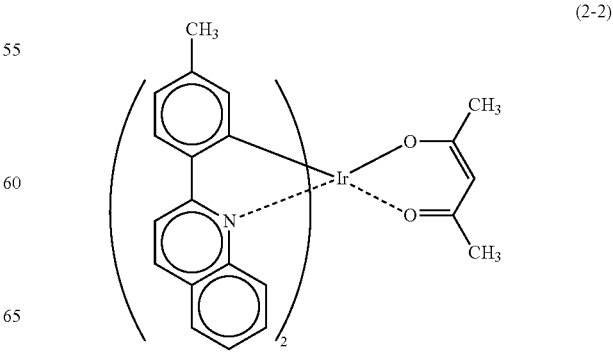

(2-2)

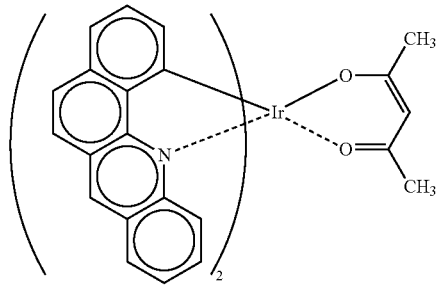
(2-3)
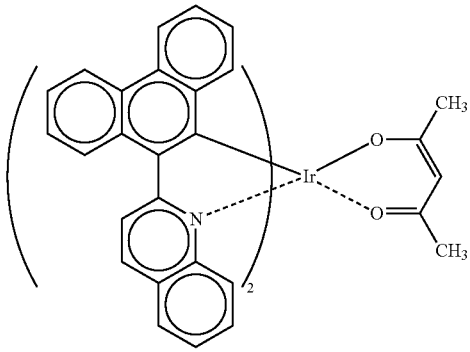
(2-7)
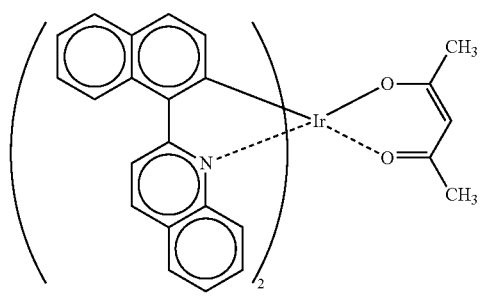
(2-4)
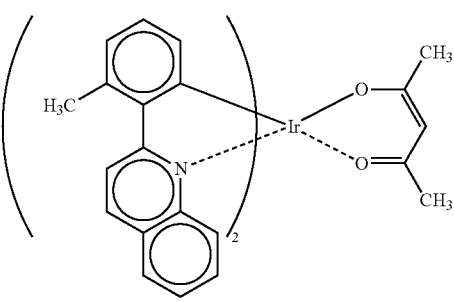
(2-8)
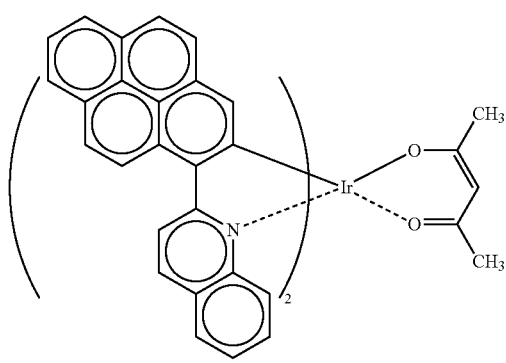
(2-5)
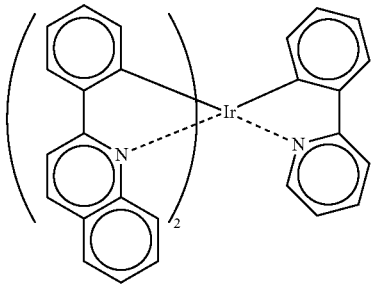
(2-9)
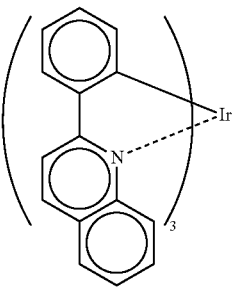
(2-10)
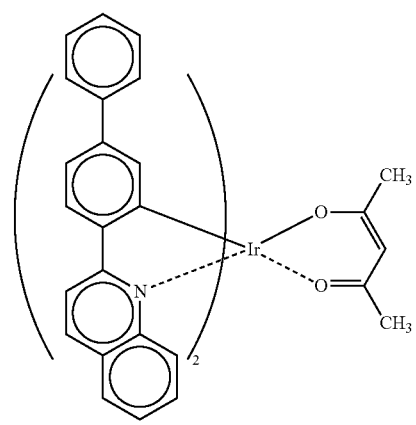
(2-6)
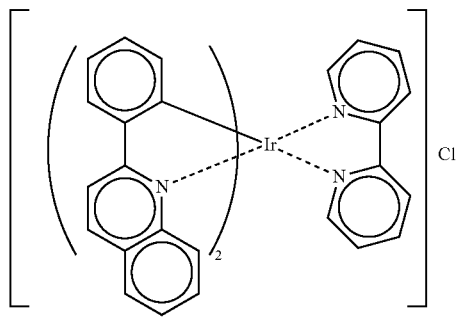
(2-11)

(2-12)
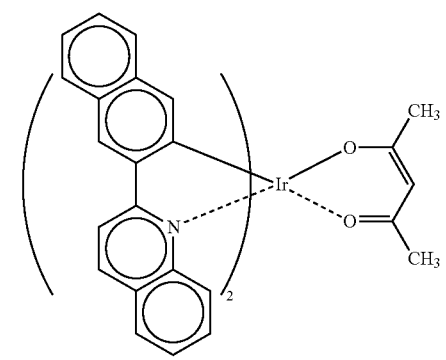

(2-13)
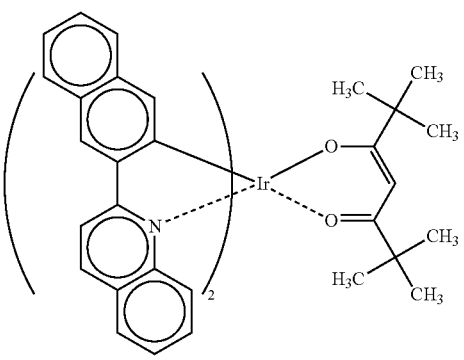

(2-14)
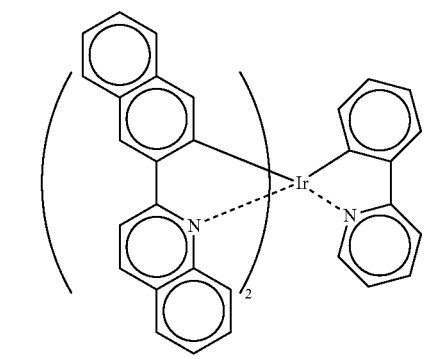

(2-15)
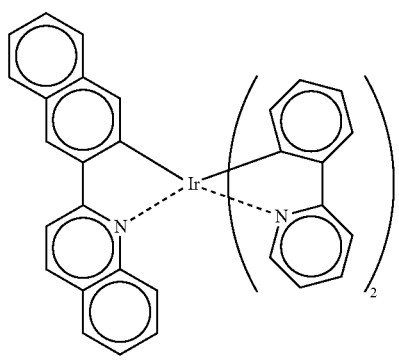

(2-16)
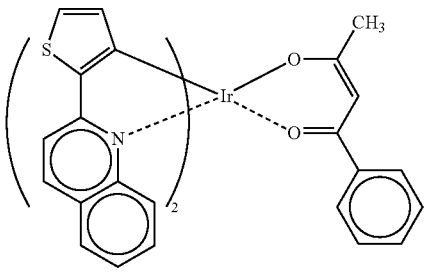

(2-17)
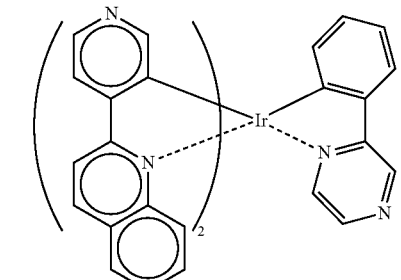

(2-18)
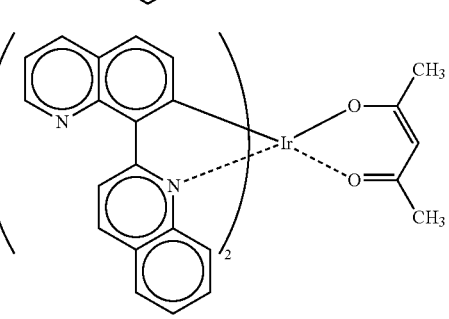

(2-19)
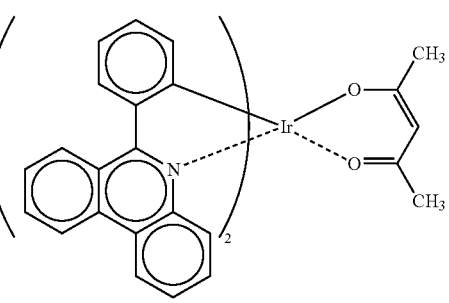

(2-20)
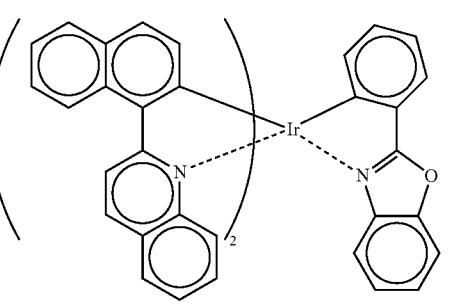

The synthesis of the compound of the invention can be accomplished by any proper method. For example, various ligands or dissociation products thereof and an iridium compound may be processed at room temperature or at elevated temperatures (heating by microwave, too, is effective besides normal heating) in the presence or absence of a solvent (e.g., halogen-based solvent, alcohol-based solvent, ether-based solvent, water) or in the presence or absence of a base (e.g., various organic bases such as sodium methoxide, t-butoxy potassium, triethylamine and potassium carbonate). As the starting materials there may be used iridium chloride (III), trisacetyl acetonate iridium (III), potassium hexachloroiridate (III), potassium hexachloroiridate (IV), and analogues thereof.

Some examples of the synthesis of the compound of the invention will be given below.

SYNTHESIS EXAMPLE 1'

Synthesis of Compound (2-1)

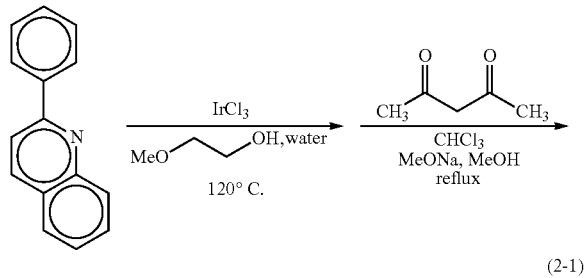

(2-1)

1 g of 2-phenylquinoline, 0.71 g of iridium chloride (III), 40 ml of 2-methoxy ethanol and 10 ml of water were mixed. The mixture was then stirred at a temperature of 120° C. in a stream of nitrogen for 6 hours. The mixture was then cooled to room temperature. To the mixture was then added 50 ml of a 1 N aqueous solution of hydrochloric acid. The solid thus precipitated was then withdrawn by filtration. The solid thus withdrawn was then purified through silica gel column chromatography (chloroform) to obtain a reddish brown solid. 0.1 g of the reddish brown solid, 0.08 g of acetyl acetone, 0.15 ml of a 28 wt-% methanol solution of sodium methoxide and 30 ml of chloroform were then mixed. The mixture was then heated under reflux for 3 hours. The mixture was then cooled to room temperature. The reaction solution was then purified through silica gel column chromatography (chloroform) to obtain 0.08 g of a red solid (2-1).

SYNTHESIS EXAMPLE 2'

Synthesis of Exemplary Compound (2-12)

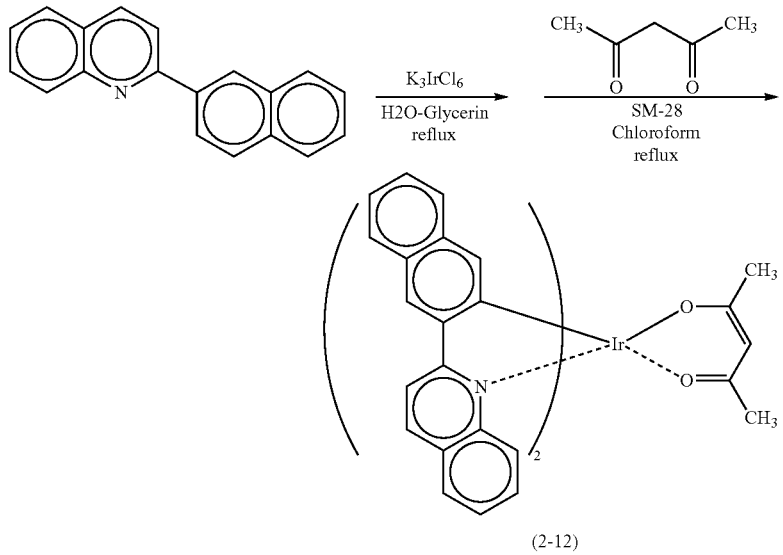

(2-12)

To a solution of 0.65 g of K$_3$IrCl$_6$ in 12 ml of water were added 0.68 g of 2-(2-naphthyl)quinoline and 50 ml of glycerin. The mixture was then heated to a temperature of 180° C. with stirring for 6 hours. After the termination of reaction, the reaction solution was then allowed to cool. To the reaction solution was then added water. The resulting brown solid was withdrawn by filtration, and then dried. Subsequently, the solid thus obtained was dissolved in 200 ml of chloroform. To the solution thus obtained were then added 2.5 g of acetyl acetone and 4.8 g of a 28% methanol solution of sodium methoxide. The reaction solution was then heated under reflux for reaction for 8 hours. After the termination of reaction, the reaction solution was then poured into 300 ml of water. The reaction solution was then extracted with chloroform. The resulting extract was dried over anhydrous magnesium sulfate, and then concentrated to obtain a solid which was then developed through silica gel column chromatography (20:1 mixture of chloroform and methanol). A red fraction thus eluted was concentrated, recrystallized from a mixture of chloroform and ethanol, and then dried to obtain 330 mg of the desired exemplary compound 2-12. The compound thus obtained was then measured for solution fluorescent spectrum. The resulting fluorescence had λmax of 658 nm (CHCl$_3$).

SYNTHESIS EXAMPLE 3'

Synthesis of Exemplary Compound (2-4)

The synthesis procedure of Synthesis Example 2' was followed except that the ligand 2-(2-naphthyl)quinoline was replaced by 2-(1-naphthyl)quinoline. Thus, the desired exemplary compound 1-4 was obtained in an amount of 57 mg. The compound thus obtained was then measured for solution fluorescent spectrum. The resulting fluorescence had λmax of 644 nm (CHCl₃).

SYNTHESIS EXAMPLE 4'

Synthesis of Exemplary Compound (2-15)

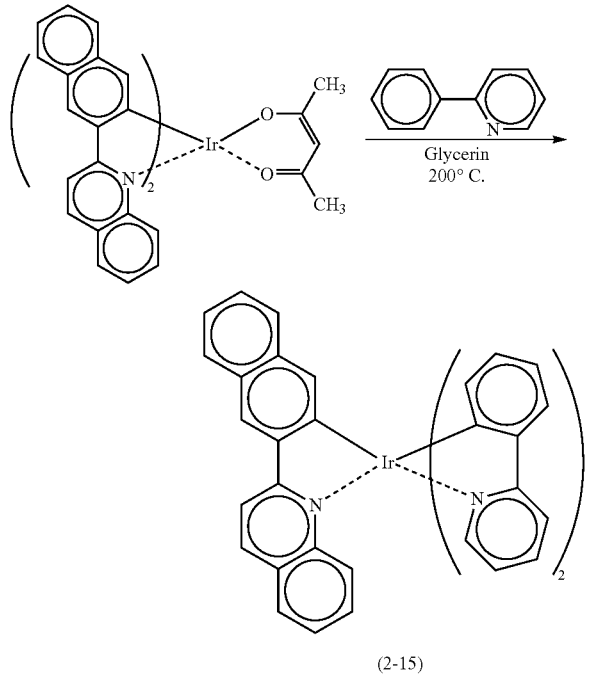

(2-15)

30 mg of the exemplary compound (2-12) of the invention and 60 mg of 2-phenylpyridine were added to 2 ml of glycerin. The mixture was then heated to 200° C. with stirring for 3 hours. After the termination of reaction, the reaction mixture was allowed to cool. To the reaction solution was then added water. The reaction solution was then extracted with chloroform. The resulting extract was dried over anhydrous magnesium sulfate, and then concentrated to obtain a solid which was then developed through silica gel column chromatography with chloroform. An orange-colored fraction thus eluted was concentrated, recrystallized from a mixture of chloroform and ethanol, and then dried to obtain 10 mg of the desired exemplary compound 2-15. The compound thus obtained was then measured for solution fluorescent spectrum. The resulting fluorescence had λmax of 646 nm (CHCl₃).

The light-emitting device comprising the compound of the invention (the first and second embodiments) will be further described hereinafter. The light-emitting device of the invention is not specifically limited in its system, driving method and form of utilization so far as it comprises the compound of the invention. In practice, however, the light-emitting device of the invention is preferably in the form of structure utilizing light emission from the compound of the invention or structure comprising the compound of the invention as a charge-transporting material. A representative example of light-emitting device is an organic EL (electroluminescence) device.

The process for the formation of the organic layer in the light-emitting device comprising the compound of the invention is not specifically limited. In practice, however, any method such as resistively-heated vacuum evaporation method, electron beam method, sputtering method, molecular lamination method, coating method, ink jet method and printing method may be used. Preferred among these methods are resistively-heated vacuum evaporation method and coating method from the standpoint of properties and producibility. More desirable among these methods is coating method from the standpoint of prevention of thermal decomposition during vacuum evaporation.

The light-emitting device of the invention comprises a light-emitting layer or a plurality of thin organic compound layers containing a light-emitting layer formed interposed between a pair of electrodes, i.e., cathode and anode. There may be provided a positive hole-injecting layer, a positive hole-transporting layer, an electron-injecting layer, an electron-transporting layer and a protective layer besides the light-emitting layer. These layers may be provided with other functions. The various layers may be each made of various materials.

The anode supplies a positive hole into the positive hole-injecting layer, positive hole-transporting layer, light-emitting layer, etc. The anode may be made of a metal, alloy, metal oxide, electrically-conductive compound or mixture thereof, preferably a material having a work function of 4 eV or more. Specific examples of such a material include electrically-conductive metal oxide such as tin oxide, zinc oxide, indium oxide and indium tin oxide (ITO), metal such as gold, silver, chromium and nickel, mixture or laminate of such a metal and electrically-conductive metal oxide, electrically inorganic material such as copper iodide and copper sulfate, electrically-conductive organic material such as polyaniline, polythiophene and polypyrrole, and laminate of these materials with ITO. Preferred among these materials are electrically-conductive metal oxides. Particularly preferred among these electrically-conductive metal oxides is ITO from the standpoint of producibility, electrical conductivity and transparency. The thickness of the anode may be properly predetermined depending on its material. In practice, however, it is preferably from 10 nm to 5 μm, more preferably from 50 nm to 1 μm, even more preferably from 100 nm to 500 nm.

The anode is normally used in the form of anode layer formed on soda-lime glass, non-alkali glass, transparent resin substrate or the like. As the glass, if used, there is preferably used non-alkali glass to reduce the amount of ions to be eluted therefrom. Soda-lime glass, if used, is preferably coated with a barrier such as silica. The thickness of the substrate is not specifically limited so far as it suffices to maintain a desired mechanical strength. In practice, however, it is normally 0.2 mm or more, preferably 0.7 mm if glass is used.

The preparation of the anode may be accomplished by any method depending on the materials used. If ITO is used, for example, electron beam method, sputtering method, resistively-heated vacuum evaporation method, chemical reaction method (sol-gel method), method involving the coating of a dispersion of indium tin oxide or the like can be used to form an anode layer.

The anode can be cleaned or otherwise treated to lower the driving voltage of the device or enhance the light emission efficiency of the device. The anode made of ITO, for example, can be effectively subjected to UV-ozone treatment, plasma treatment, etc.

The cathode supplies electron into the electron-injecting layer, electron-transporting layer, light-emitting layer, etc. The cathode is selected taking into account the adhesivity to the layer adjacent to the negative electrode such as electron-injecting layer, electron-transporting layer and light-emitting layer, ionization potential, stability, etc. As the material constituting the cathode there may be used a metal, alloy, metal halide, metal oxide, electrically-conductive compound or mixture thereof. Specific examples of such a material include alkaline metal (e.g., Li, Na, K), fluoride thereof, alkaline earth metal (e.g., Mg, Ca), fluoride thereof, gold, silver, lead, aluminum, sodium-potassium alloy, mixture thereof, lithium-aluminum alloy, mixture thereof, magnesium-silver alloy, mixture thereof, and rare earth metal such as indium and ytterbium. Preferred among these materials are those having a work function of 4 eV or less. Even more desirable among these materials are aluminum, lithium-aluminum alloy, mixture thereof, magnesium-silver alloy, and mixture thereof. The cathode may be not only in the form of single layer structure comprising the foregoing compound or mixture but also in the form of laminated structure comprising the foregoing compound or mixture. The thickness of the cathode may be properly predetermined depending on its material. In practice, however, it is preferably from 10 nm to 5 μm, more preferably from 50 nm to 1 μm, even more preferably from 100 nm to 1 μm.

The preparation of the cathode can be accomplished by any method as electron beam method, sputtering method, resistively-heated vacuum evaporation method and coating method. A single metal may be vacuum-vaporized. Alternatively, two or more components may be vacuum-vaporized at the same time. Further, a plurality of metals may be vacuum-vaporized to form an alloy electrode. Alternatively, an alloy which has been previously prepared may be vacuum-vaporized.

The sheet resistivity of the anode and cathode is preferably as low as possible and thus is preferably hundreds of ohm/□ or less.

As the material constituting the light-emitting layer there may be used any material which can form a layer capable of injecting positive hole from the anode, positive hole-injecting layer or positive hole-transporting layer as well as injecting electron from the cathode, electron-injecting layer or electron-transporting layer during the application of electric field, moving electron thus injected or providing a site for the recombination of positive hole and electron for emission of light. Alternatively, any material which emits light from either singlet exciton or triplet exciton may be used. Examples of the light-emitting material employable herein include various metal complexes such as metal complex and rare earth complex of benzoxazole derivative, benzoimidazole derivative, benzothiazole derivative, styrylbenzene derivative, polyphenyl derivative, diphenylbutadiene derivative, tetraphenylbutadiene derivative, naphthalimide derivative, coumarine derivative, perylene derivative, perynone derivative, oxadiazole derivative, aldazine derivative, pyralidine derivative, cyclopentadiene derivative, bisstyrylanthracene derivative, quinacridone derivative, pyrrolopyridine derivative, thiadiazolopyridine derivative, cyclopentadiene derivative, styrylamine derivative, aromatic dimethylidine compound and 8-quinolinol derivative, polymer compound such as polythiophene, polyphenylene and polyphenylenevinylene, organic silane derivative, and the compound of the invention. The thickness of the light-emitting layer is not specifically limited but is normally from 1 nm to 5 μm, preferably from 5 nm to 1 μm, even more preferably from 10 nm to 500 nm.

The process for the formation of the light-emitting layer is not specifically limited. In practice, however, any method such as resistively-heated vacuum evaporation method, electron beam method, sputtering method, molecular lamination method, coating method (e,g, spin coating method, casting method, dip coating method), ink jet method, LB method and printing method may be used. Preferred among these methods are resistively-heated vacuum evaporation method and coating method.

As the material constituting the positive hole-injecting layer and positive hole-transporting layer there may be used any material having any of capability of injecting positive hole from the anode, capability of transporting positive hole and capability of giving barrier to electron injected from the cathode. Specific examples of such a material include electrically-conductive polymer oligomers such as carbazole derivative, triazole derivative, oxazole derivative, oxadiazole derivative, imidazole derivative, polyarylalkane derivative, pyrazoline derivative, pyrazolone derivative, phenylenediamine derivative, arylamine derivative, amino-substituted chalcone derivative, styrylanthracene derivative, fluorenone derivative, hydrazone derivative, stilbene derivative, silazane derivative, aromatic tertiary amine compound, styrylamine compound, aromatic dimethylidine compound, porphyrin compound, polysilane compound, poly(N-vinylcarbazole) derivative, aniline copolymer, thiophene oligomer and polythiophene, organic silane derivative, carbon film, and the compound of the invention. The thickness of the positive hole-injecting layer and positive hole-transporting layer is not specifically limited but is preferably from 1 nm to 5 μm, more preferably from 5 nm to 1 μm, even more preferably from 10 nm to 500 nm. The positive hole-injecting layer and positive hole-transporting layer each may be in the form of single layer structure made of one or more of the foregoing material or multi-layer structure consisting of a plurality of layers having the same or different compositions.

The formation of the positive hole-injecting layer and positive hole-transporting layer can be accomplished by any method such as vacuum evaporation method, LB method, method involving the coating of a solution or dispersion of the foregoing positive hole-injecting or transporting material in a solvent (e.g., spin coating method, casting method, dip coating method), ink jet method and printing method. In the case of coating method, the foregoing positive hole-injecting or transporting material may be dissolved or dispersed in a solvent with a resin component. Examples of such a resin component include polyvinyl chloride, polycarbonate, polystyrene, polymethylmethacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin, and silicon resin.

As the material constituting the electron-injecting material layer and electron-transporting layer there may be used any material having any of capability of injecting electron from the cathode, capability of transporting electron and capability of giving barrier to positive hole injected from the anode. Specific examples of such a material include various metal complexes such as metal complex of heterocyclic tetracarboxylic anhydride such as triazole derivative, oxazole derivative, oxadiazole derivative, fluorenone derivative, anthraquinodimethane derivative, anthrone derivative, diphenylquinone derivative, thiopyranedioxide derivative, carbodiimide derivative, fluorenilidenemethane derivative, distyrylpyrazine derivative and naphthaleneperylene, phthalocyanine derivative and 8-quinolinol derivative and metal complex comprising metal phthalocyanine, benzoxazole or benzothiazole as a ligand, organic silane derivative, and the compounds of the present invention. The thickness of the electron-injecting layer and electron-transporting layer is not specifically limited but is preferably from 10 nm to 500 nm, more preferably from 5 nm to 1 μm, even more preferably from 10 nm to 500 nm. The electron-injecting layer and electron-transporting layer each may be in the form of single layer structure made of one or more of the foregoing material or multi-layer structure consisting of a plurality of layers having the same or different compositions.

The formation of the electron-injecting layer and electron-transporting layer can be accomplished by any method such as vacuum evaporation method, LB method, method involving the coating of a solution or dispersion of the foregoing positive hole-injecting or transporting material in a solvent (e.g., spin coating method, casting method, dip coating method), ink jet method and printing method. In the case of coating method, the foregoing positive hole-injecting or transporting material may be dissolved or dispersed in a solvent with a resin component. As the resin component there may be used any of those exemplified with reference to the positive hole-injecting or transporting layer.

As the material constituting the protective layer there may be used any material capable of preventing materials which accelerating the deterioration of the device such as water content and oxygen from entering into the device. Specific examples of such a material include metal such as In, Sn, Pb, Au, Cu, Ag, Al, Ti and Ni, metal oxide such as MgO, SiO, $SiO_2$, $Al_2O_3$, GeO, NiO, CaO, BaO, $Fe_2O_2$, $Y_2O_3$ and $TiO_2$, metal fluoride such as $MgF_2$, LiF, $AlF_3$ and $CaF_2$, polyethylene, polypropylene, polymethyl methacrylate, polyimide, polyurea, polytetrafluoroethylene, polychlorotrifluoroethylene, polydichlorofluoroethylene, polymer of chlorotrifluoroethylene with dichlorodifluoroethylene, copolymer obtained by the copolymerization of tetrafluoroethylene with a monomer mixture comprising at least one comonomer, fluorine-containing copolymer having a cyclic structure in the copolymer main chain, water-absorbing material having a water absorption of 1% or more, and moisture-resistant material having a water absorption of 0.1% or less.

The process for the formation of the protective layer is not specifically limited. Examples of the method employable herein include vacuum evaporation method, sputtering method, reactive sputtering method, MBE (molecular beam epitaxy) method, cluster ion beam method, ion plating method, plasma polymerization method (high frequency excited ion plating method), plasma CVD method, laser CVD method, heat CVD method, gas source CVD method, coating method, and printing method.

Specific embodiments of implication of the invention will be described hereinafter, but the present invention should not be construed as being limited thereto.

COMPARATIVE EXAMPLE 1

40 mg of a poly(N-vinylcarbazole), 12 mg of PBD(2-(4-biphenyl)-5-(4-t-butylphenyl)-1,3,4-oxadiazole) and 1 mg of the following compound A were dissolved in 2.5 ml of dichloroethane. The solution thus obtained was then spin-coated onto a substrate which had been cleaned (1,500 rpm, 20 sec). The thickness of the organic layer thus formed was 98 nm. A patterned mask (arranged such that the light-emitting area was 4 mm×5 mm) was then disposed on the thin organic layer. Magnesium and silver were then simultaneously vacuum-evaporated onto the thin organic layer at a ratio of 10:1 to a thickness of 50 nm in a vacuum metallizer. Silver was then vacuum-evaporated onto the metal deposit to a thickness of 50 nm. Using a Type 2400 source measure unit produced by TOYO TECHNICA CO., LTD., a dc constant voltage was then applied to the EL device thus prepared to cause the emission of light which was then measured for luminance and wavelength by means of a Type BM-8 luminance meter produced by TOPCON CORP. and a Type PMA-11 spectral analyzer produced by Hamamatsu Photonics Co., Ltd., respectively. As a result, it was found that green light having λmax of 500 nm had been emitted. The external quantum yield around 100 cd/m² was then calculated. The results were 0.1%. The specimen was then allowed to stand in a nitrogen atmosphere for 1 hour. As a result, the specimen was visually observed to have numerous dark spots on the light-emitting surface thereof.

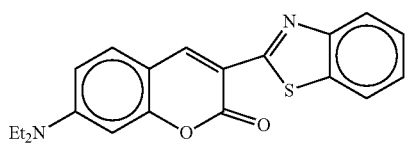

Compound A

Example 1

A device was prepared in the same manner as in Comparative Example 1 except that the compound (1-1) was used instead of the compound A. As a result, green light having λmax of 510 nm was emitted. The external quantum yield around 100 cd/m² was 2.9%. The specimen was then allowed to stand in a nitrogen atmosphere for 1 hour. As a result, the specimen was visually observed to have a small number of dark spots on the light-emitting surface thereof.

Example 2

A device was prepared in the same manner as in Comparative Example 1 except that the compound (1-2) was used instead of the compound A. As a result, green light having λmax of 510 nm was emitted. The specimen was then allowed to stand in a nitrogen atmosphere for 1 hour. As a result, the specimen was visually observed to have no dark spots on the light-emitting surface thereof.

Example 3

A device was prepared in the same manner as in Comparative Example 1 except that the compound (1-3) was used instead of the compound A. As a result, orange-colored light having λmax of 590 nm was emitted. The specimen was then allowed to stand in a nitrogen atmosphere for 1 hour. As a result, the specimen was visually observed to have no dark spots on the light-emitting surface thereof.

Example 4

A device was prepared in the same manner as in Comparative Example 1 except that the compound (1-4) was used instead of the compound A. As a result, green light having λmax of 510 nm was emitted. The specimen was then allowed to stand in a nitrogen atmosphere for 1 hour. As a result, the specimen was visually observed to have no dark spots on the light-emitting surface thereof.

Example 5

A device was prepared in the same manner as in Comparative Example 1 except that the compound (1-20) was used instead of the compound A. As a result, green light having λmax of 547 nm was emitted. The specimen was then allowed to stand in a nitrogen atmosphere for 1 hour. As a result, the specimen was visually observed to have no dark spots on the light-emitting surface thereof.

Example 6

A device was prepared in the same manner as in Comparative Example 1 except that the compound (1-24) was used instead of the compound A. As a result, green light having λmax of 530 nm was emitted. The specimen was then allowed to stand in a nitrogen atmosphere for 1 hour. As a result, the specimen was visually observed to have no dark spots on the light-emitting surface thereof.

Example 7

A device was prepared in the same manner as in Comparative Example 1 except that the compound (1-25) was used instead of the compound A. As a result, light having λmax of 564 nm was emitted. The specimen was then allowed to stand in a nitrogen atmosphere for 1 hour. As a result, the specimen was visually observed to have no dark spots on the light-emitting surface thereof.

Example 8

A device was prepared in the same manner as in Comparative Example 1 except that the compound (1-36) was used instead of the compound A. As a result, green light having λmax of 520 nm was emitted. The specimen was then allowed to stand in a nitrogen atmosphere for 1 hour. As a result, the specimen was visually observed to have no dark spots on the light-emitting surface thereof.

Example 9

A device was prepared in the same manner as in Comparative Example 1 except that the compound (1-41) was used instead of the compound A. As a result, green light having λmax of 513 nm was emitted. The external quantum yield around 100 cd/m" was 5.1%. The specimen was then allowed to stand in a nitrogen atmosphere for 1 hour. As a result, the specimen was visually observed to have no dark spots on the light-emitting surface thereof.

Example 10

A device was prepared in the same manner as in Comparative Example 1 except that the compound (1-42) was used instead of the compound A. As a result, green light having λmax of 535 nm was emitted. The specimen was then allowed to stand in a nitrogen atmosphere for 1 hour. As a result, the specimen was visually observed to have no dark spots on the light-emitting surface thereof.

Example 11

A device was prepared in the same manner as in Comparative Example 1 except that the compound (1-44) was used instead of the compound A. As a result, orange-colored light having λmax of 532 nm was emitted. The specimen was then allowed to stand in a nitrogen atmosphere for 1 hour. As a result, the specimen was visually observed to have no dark spots on the light-emitting surface thereof.

Example 12

A device was prepared in the same manner as in Comparative Example 1 except that the compound (1-46) was used instead of the compound A. As a result, yellow light having λmax of 568 nm was emitted. The specimen was then allowed to stand in a nitrogen atmosphere for 1 hour. As a result, the specimen was visually observed to have no dark spots on the light-emitting surface thereof.

Example 13

A device was prepared in the same manner as in Comparative Example 1 except that the compound (1-65) was used instead of the compound A. As a result, yellowish orange-colored light having λmax of 578 nm was emitted. The specimen was then allowed to stand in a nitrogen atmosphere for 1 hour. As a result, the specimen was visually observed to have no dark spots on the light-emitting surface thereof.

Example 14

A device was prepared in the same manner as in Comparative Example 1 except that the compound (1-66) was used instead of the compound A. As a result, reddish orange-colored light having λmax of 625 nm was emitted. The specimen was then allowed to stand in a nitrogen atmosphere for 1 hour. As a result, the specimen was visually observed to have no dark spots on the light-emitting surface thereof.

Example 15

An ITO substrate which had been cleaned was put in a vacuum metallizer. α-NPD(N,N'-diphenyl-N,N'-di(α-naphthyl)-benzidine) was then vacuum-evaporated onto the ITO substrate to a thickness of 40 nm. The following compound B and the compound (1-46) of the invention were then simultaneously vacuum-evaporated onto the substrate at a ratio of 10:1 to a thickness of 24 nm. The following compound C was then vacuum-evaporated onto the substrate to a thickness of 24 nm. A patterned mask (arranged such that the light-emitting area was 4 mm×5 mm) was then disposed on the thin organic layer. Magnesium and silver were then simultaneously vacuum-evaporated onto the thin organic layer at a ratio of 10:1 to a thickness of 250 nm in the vacuum metallizer. Silver was then vacuum-evaporated onto the metal deposit to a thickness of 250 nm. A dc constant voltage was then applied to the EL device thus prepared to cause the emission of light. As a result, it was found that yellow light having λmax of 567 nm had been emitted and the external quantum efficiency had been 13.6% (185 cd/m$^2$·hr).

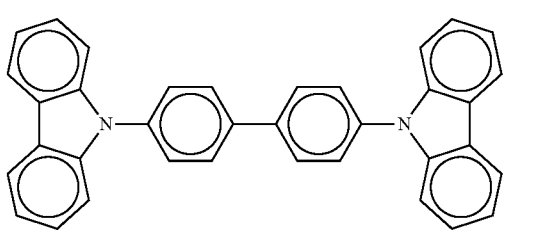

(Compound B)

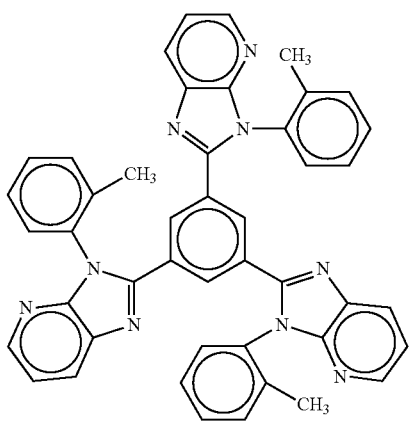
(Compound C)

Example 16

An ITO substrate which had been cleaned was put in a vacuum metallizer. α-NPD(N,N'-diphenyl-N,N'-di(α-naphthyl)-benzidine) was then vacuum-evaporated onto the ITO substrate to a thickness of 40 nm. The compound (1-42) of the invention were then vacuum-evaporated onto the substrate to a thickness of 20 nm. The compound C was then vacuum-evaporated onto the substrate to a thickness of 40 nm. A patterned mask (arranged such that the light-emitting area was 4 mm×5 mm) was then disposed on the thin organic layer. Magnesium and silver were then simultaneously vacuum-evaporated onto the thin organic layer at a ratio of 10:1 to a thickness of 250 nm in the vacuum metallizer. Silver was then vacuum-evaporated onto the metal deposit to a thickness of 250 nm. A dc constant voltage was then applied to the EL device thus prepared to cause the emission of light. As a result, it was found that greenish yellow light having λmax of 535 nm had been emitted and the external quantum efficiency had been 3.1% (120 cd/m²·hr).

Example 17

40 mg of a poly(N-vinylcarbazole), 12 mg of PBD(2-(4-biphenyl)-5-(4-t-butylphenyl)-1,3,4-oxadiazole) and 1 mg of the compound (1-4) of the invention were dissolved in 2.5 ml of dichloroethane. The solution thus obtained was then spin-coated onto a substrate which had been cleaned (1,500 rpm, 20 sec). The thickness of the organic layer thus formed was 98 nm. The compound C was then vacuum-evaporated onto the organic layer to a thickness of 40 nm in a vacuum metallizer. A patterned mask (arranged such that the light-emitting area was 4 mm×5 mm) was then disposed on the thin organic layer. Lithium fluoride was then vacuum-evaporated onto the material to a thickness of 5 nm in the vacuum metallizer. Aluminum was then vacuum-evaporated onto the material to a thickness of 500 nm. A dc constant voltage was then applied to the EL device thus prepared to cause the emission of light. As a result, it was found that orange-colored light having λmax of 580 nm had been emitted. The external quantum efficiency was 4.2% (1,000 cd/m²).

Example 18

Baytron P (PEDOT-PSS solution (polyethylene dioxythiophene-polystyrenesulfonic acid-doped material) produced by Bayer Inc.) was spin-coated onto a substrate which had been cleaned (1,000 rpm, 30 sec), and then dried at a temperature of 150° C. in vacuo for 1.5 hours. The thickness of the organic layer thus formed was 70 nm. 40 mg of a poly(N-vinylcarbazole) and 1 mg of the compound (1-42) of the invention were dissolved in 2.5 ml of dichloroethane. The solution thus obtained was then spin-coated onto the foregoing substrate which had been cleaned (1,500 rpm, 20 sec). A patterned mask (arranged such that the light-emitting area was 4 mm×5 mm) was then disposed on the thin organic layer. Magnesium and silver were then simultaneously vacuum-evaporated onto the thin organic layer at a ratio of 10:1 to a thickness of 250 nm in a vacuum metallizer. Silver was then vacuum-evaporated onto the metal deposit to a thickness of 250 μm. A dc constant voltage was then applied to the EL device thus prepared to cause the emission of light. As a result, it was found that yellowish green light having λmax of 540 nm had been emitted. The external quantum efficiency was 6.2% (2,000 cd/m²).

EL devices comprising compounds of the invention were prepared and evaluated in the same manner as mentioned above. As a result, high efficiency EL devices capable of emitting light having various colors were prepared. These EL devices were confirmed to have excellent durability. Further, vacuum-metallized doped devices comprising compounds of the invention can emit light at a high efficiency. Devices comprising a single layer made of a light-emitting material of the invention, too, can emit light at a high efficiency.

The compound of the invention can be used as an organic EL material. The compound of the invention can also be used to prepare a high efficiency and durability EL device capable of emitting light having various colors.

COMPARATIVE EXAMPLE 2

α-NPD(N,N'-diphenyl-N,N'-di(α-naphthyl)-benzidine) was vacuum-evaporated onto an ITO substrate which had been cleaned to a thickness of 40 nm. The following compounds A' and B' were then simultaneously vacuum-evaporated onto the substrate at a ratio of 10:1 to a thickness of 24 nm. The compound C' was then vacuum-evaporated onto the metal deposit. A patterned mask (arranged such that the light-emitting area was 4 mm×5 mm) was then disposed on the thin organic layer. Magnesium and silver were then simultaneously vacuum-evaporated onto the thin organic layer at a ratio of 10:1 to a thickness of 250 nm in a vacuum metallizer. Silver was then vacuum-evaporated onto the metal deposit to a thickness of 50 nm. Using a Type 2400 source measure unit produced by TOYO TECHNICA CO., LTD., a dc constant voltage was then applied to the EL device thus prepared to cause the emission of light which was then measured for luminance and wavelength by means of a Type BM-8 luminance meter produced by TOPCON CORP. and a Type PMA-11 spectral analyzer produced by Hamamatsu Photonics Co., Ltd., respectively. As a result, it was found that green light having λmax of 516 nm and CIE chromaticity value (x, y) of 0.29 and 0.62 had been emitted. The external quantum efficiency was 13.6% (478 cd/m2).

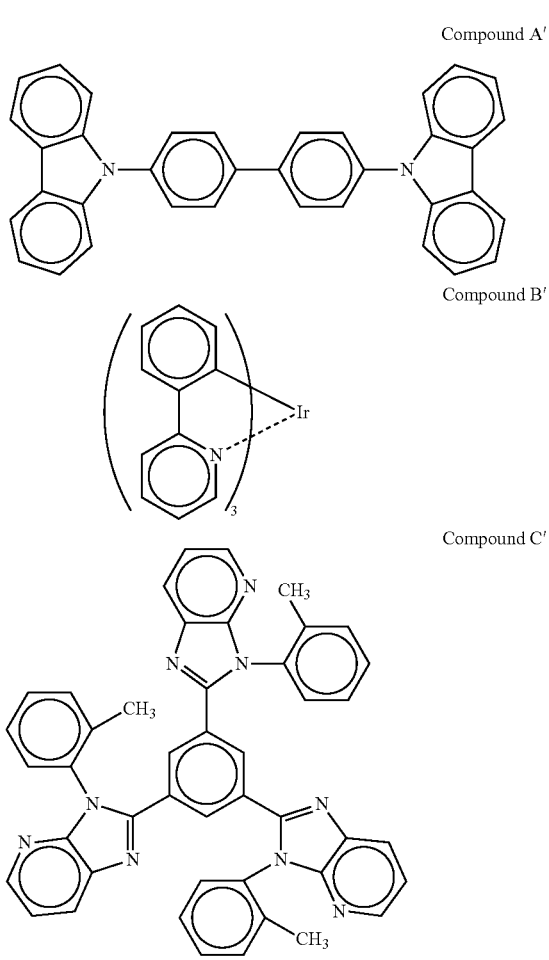

Compound A'

Compound B'

Compound C'

COMPARATIVE EXAMPLE 3

α-NPD (N,N'-diphenyl-N,N'-di(α-naphthyl)-benzidine) was vacuum-evaporated onto an ITO substrate which had been cleaned to a thickness of 40 nm. Alq (trisquinonate aluminum) and DCM(4-(Dicyanomethylene)-2-methyl-6-(4-dimethylamino styryl)-4H-pyran) were then simultaneously vacuum-evaporated onto the substrate at a ratio of 100:1 to a thickness of 60 nm. The substrate was then cathodically vacuum-metallized in the same manner as in Comparative Example 1 to prepare a device. As a result, reddish orange-colored light having λmax of 597 nm and CIE chromaticity value (x, y) of 0.54 and 0.44 had been emitted. The external quantum efficiency was 0.89% (248 cd/m$^2$). The half width of emission spectrum was 92 nm.

Example 19

A device was prepared in the same manner as in Comparative Example 2 except that the compound (2-1) was used instead of the compound B'. As a result, red light having λmax of 599 nm and CIE chromaticity value (x, y) of 0.60 and 0.39 had been emitted. The external quantum efficiency was 13.4% (252 cd/m$^2$). The half width of emission spectrum was 69 nm.

Example 20

A device was prepared in the same manner as in Comparative Example 2 except that the compound (2-12) was used instead of the compound B'. As a result, red light having λmax of 623 nm and CIE chromaticity value (x, y) of 0.65 and 0.34 had been emitted. The external quantum efficiency was 10.9% (379 cd/m$^2$). The half width of emission spectrum was 75 nm.

Example 21

40 mg of a poly(N-vinylcarbazole), 12 mg of PBD(2-(4-biphenyl)-5-(4-t-butylphenyl)-1,3,4-oxadiazole) and 1 mg of the compound (2-1) of the invention were dissolved in 2.5 ml of dichloroethane. The solution thus obtained was then spin-coated onto a substrate which had been cleaned (1,500 rpm, 20 sec). The thickness of the organic layer thus formed was 20 nm. A patterned mask (arranged such that the light-emitting area was 4 mm×5 mm) was then disposed on the thin organic layer. Magnesium and silver were then simultaneously vacuum-evaporated onto the thin organic layer at a ratio of 10:1 to a thickness of 250 nm in a vacuum metallizer. Silver was then vacuum-evaporated onto the metal deposit to a thickness of 250 nm. A dc constant voltage was then applied to the EL device thus prepared to cause the emission of light which was then measured for luminance, emission spectrum and voltage-current characteristics. As a result, it was found that orange-colored light having λmax of 603 nm and chromaticity value (x, y) of 0.61 and 0.38 had been emitted. The external quantum yield around 50 cd/m$^2$ was then calculated. The results were 5.0%.

Example 22

A device was prepared in the same manner as in Example 21 except that the compound (2-4) was used instead of the compound (2-1). As a result, red light having λmax of 641 nm and CIE chromaticity value (x, y) of 0.68 and 0.30 had been emitted. The external quantum yield around 50 cd/m$^2$ was calculated. The results were 5.2%.

Example 23

40 mg of a poly(N-vinylcarbazole), 12 mg of PBD(2-(4-biphenyl)-5-(4-t-butylphenyl)-1,3,4-oxadiazole) and 1 mg of the compound (2-12) of the invention were dissolved in 2.5 ml of dichloroethane. The solution thus obtained was then spin-coated onto a substrate which had been cleaned (1,500 rpm, 20 sec). The thickness of the organic layer thus formed was 110 nm. The compound C' was then vacuum-evaporated onto the organic layer to a thickness of 40 nm in a vacuum metallizer. A patterned mask (arranged such that the light-emitting area was 4 mm×5 mm) was then disposed on the thin organic layer. Lithium fluoride was then vacuum-evaporated onto the thin organic layer to a thickness of 5 nm in the vacuum metallizer. Aluminum was then vacuum-evaporated onto the metal deposit to a thickness of 500 nm. A dc constant voltage was then applied to the EL device thus prepared to cause the emission of light. As a result, it was found that red light having λmax of 633 nm had been emitted. The external quantum efficiency was 6.2% (1,000 cd/m$^2$).

Example 24

40 mg of a poly(N-vinylcarbazole), 12 mg of the following compound D' and 1 mg of the compound (2-12) of the invention were dissolved in 2.5 ml of dichloroethane. The solution thus obtained was then spin-coated onto a substrate which had been cleaned (3,000 rpm, 20 sec). The substrate was then heated and dried in vacuo (100° C., 1 hour). A solution of the compound C' in 2.5 ml of n-butanol was then spin-coated onto the substrate. The thickness of the organic layer thus formed was 130 nm. A patterned mask (arranged such that the light-emitting area was 4 mm×5 mm) was then disposed on the thin organic layer. Lithium fluoride was then vacuum-evaporated onto the thin organic layer to a thickness of 5 nm in the vacuum metallizer. Aluminum was then vacuum-evaporated onto the metal deposit to a thickness of 500 nm. A dc constant voltage was then applied to the EL device thus prepared to cause the emission of light. As a result, it was found that red light having λmax of 635 nm had been emitted. The external quantum efficiency was 6.8% (2,000 cd/m$^2$).

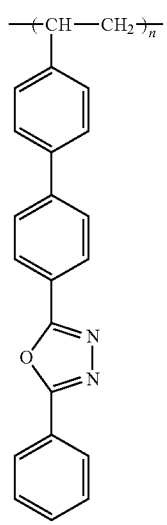

Compound D'

Weight-average molecular weight: 20,000 (polystyrene equivalence)

Example 25

A device was prepared in the same manner as in Comparative Example 1 except that the compound (1-33) was used instead of the Compound A of Comparative Example 1. As a result, green light was emitted. The specimen was then allowed to stand in a nitrogen atmosphere for 1 hour. As a result, the specimen was visually observed to have no dark spots on the light-emitting surface thereof.

Example 26

A device was prepared in the same manner as in Comparative Example 1 except that the compound (1-38) was used instead of the Compound A of Comparative Example 1. As a result, green light was emitted. The specimen was then allowed to stand in a nitrogen atmosphere for 1 hour. As a result, the specimen was visually observed to have no dark spots on the light-emitting surface thereof.

Example 27

A device was prepared in the same manner as in Comparative Example 1 except that the compound (1-56) was used instead of the Compound A of Comparative Example 1. As a result, red light was emitted. The specimen was then allowed to stand in a nitrogen atmosphere for 1 hour. As a result, the specimen was visually observed to have no dark spots on the light-emitting surface thereof.

Example 28

A device was prepared in the same manner as in Comparative Example 1 except that the compound (2-9) was used instead of the Compound A of Comparative Example 1. As a result, red light was emitted. The specimen was then allowed to stand in a nitrogen atmosphere for 1 hour. As a result, the specimen was visually observed to have no dark spots on the light-emitting surface thereof.

EL devices comprising compounds of the invention can be prepared and evaluated in the same manner as mentioned above. Thus, high efficiency red light-emitting devices can be prepared.

The high efficiency red light-emitting device according to the invention has a higher efficiency than the conventional red light-emitting devices. Thus, the high efficiency red light-emitting device according to the invention is suitable for various arts such as display device, display, backlight, electrophotography, illuminating light source, recording light source, exposure light source, reading light source, sign, advertising display and interior. The high efficiency red light-emitting device according to the invention can consume a drastically reduced power as compared with the conventional red light-emitting organic EL devices having an external quantum yield of less than 5%. The high efficiency red light-emitting device according to the invention can also have an increased working area and be used over an extended period of time. Thus, the high efficiency red light-emitting device according to the invention can find wider application in the art of organic EL color display.

The compound of the invention can be used for medical use or as fluorescent brightening agent, photographic material, UV-absorbing material, laser dye, color filter dye, color conversion filter, etc.

The entire disclosure of each and every foreign patent application from which the benefit of foreign priority has been claimed in the present application is incorporated herein by reference, as if fully set forth.

We claim:

1. A synthesis method of a compound represented by following formula (24), the method comprising:
reacting at least one of a ligand and a dissociation product thereof with an iridium compound at a room temperature or at an elevated temperatures in the presence or absence of a solvent or in the presence or absence of a base:

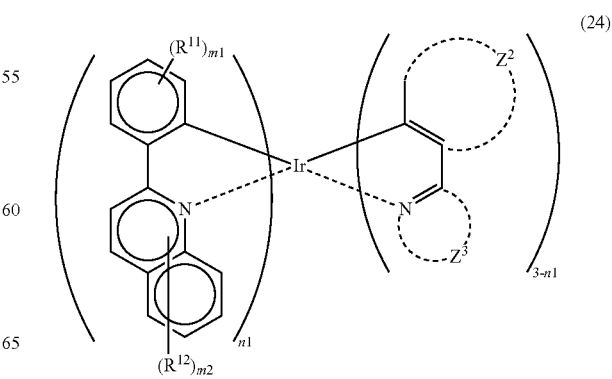

(24)

wherein $R^{11}$ and $R^{12}$ each represents an alkyl group, an aryl group, a heteroaryl group, an alkoxy group, a halogen atom, a cyano group, or a cyclic structure obtained by the connection of one of the plurality of $R^{11}$s to another of the plurality of $R^{11}$s, or one of the plurality of $R^{12}$s to another of the plurality of $R^{12}$s, or one of the plurality of $R^{11}$s, or one of the plurality of $R^{12}$s; $m^1$ represents an integer of from 0 to 4; $m^2$ represents an integer of from 0 to 6; $Z^2$ represents an atomic group which forms an aryl ring having 6 to 30 carbon atoms or a heteroaryl ring having from 2 to 30 carbon atoms and comprising a nitrogen atom, an oxygen atom, or a sulfur atom; $Z^3$ represents an atomic group which forms a nitrogen-containing heteroaryl ring having 2 to 30 carbon atoms; and $n^1$ represents an integer of from 1 or 2.

2. The synthesis method according to claim 1, which uses a mixed solvent of 2-methoxyethanol and water as the solvent.

3. The synthesis method according to claim 1, wherein the reaction is conducted in a stream of nitrogen.

4. The synthesis method according to claim 1, further comprising:
   processing with an aqueous solution of hydrochloric acid.

5. The synthesis method according to claim 1, further comprising:
   purifying through a silica gel column chromatography.

6. The synthesis method according to claim 1, which uses sodium methoxide as the base.

* * * * *